(12) United States Patent
Couch et al.

(10) Patent No.: US 10,130,503 B2
(45) Date of Patent: Nov. 20, 2018

(54) CONICAL PORT

(76) Inventors: Christopher John Couch, Karnup (AU); Robert Charles Patrick Hills, Waikiki (AU)

( * ) Notice: Subject to any disclaimer, the term of this patent is extended or adjusted under 35 U.S.C. 154(b) by 1331 days.

(21) Appl. No.: 13/824,131

(22) PCT Filed: Sep. 19, 2011

(86) PCT No.: PCT/AU2011/001204
§ 371 (c)(1),
(2), (4) Date: Jun. 10, 2013

(87) PCT Pub. No.: WO2012/034193
PCT Pub. Date: Mar. 22, 2012

(65) Prior Publication Data
US 2013/0289338 A1    Oct. 31, 2013

(30) Foreign Application Priority Data
Sep. 17, 2010    (AU) ................. 2010904201

(51) Int. Cl.
*A61F 5/00* (2006.01)
*A61M 39/02* (2006.01)
(Continued)

(52) U.S. Cl.
CPC ....... *A61F 5/0056* (2013.01); *A61M 39/0247* (2013.01); *A61B 17/0057* (2013.01);
(Continued)

(58) Field of Classification Search
CPC ...... A61M 39/0247; A61M 2039/0261; A61M 2039/0273; A61M 2039/0282;
(Continued)

(56) References Cited

U.S. PATENT DOCUMENTS 4,393,873 A    7/1983    Nawash et al.
4,743,231 A    5/1988    Kay et al.
(Continued)

FOREIGN PATENT DOCUMENTS

WO    93/08729 A1    5/1993
WO    01/72209 A1    10/2001

*Primary Examiner* — Theodore Stigell
(74) *Attorney, Agent, or Firm* — Rothwell, Figg, Ernst & Manbeck, P.C.

(57) ABSTRACT

An access port comprising a port body and a catheter, the port body defining a cavity into which a fluid can be delivered or extracted through one side of the port body, the catheter being in communication with the cavity and being disposed on an opposed side of the port body, thus protecting the catheter from needle stick damage. An access port comprising a port body and a catheter, the port body defining a cavity into which a fluid can be delivered or extracted from through one side of the port body, the port body being configured to extend partly through a hole in the body of a patient in which the access port is implanted and thus plug the said hole. The port body comprising integral means for anchoring the port body to the body of the patient. Also is provided a method for anchoring the access port to the hole and extracting the access port from the hole as well as the applicator, extractor and delivery sheath for anchoring and extracting the access port.

21 Claims, 15 Drawing Sheets

(51) Int. Cl.
    *A61B 17/00* (2006.01)
    *A61B 17/02* (2006.01)
(52) U.S. Cl.
    CPC .. *A61B 17/0293* (2013.01); *A61M 2039/0261* (2013.01); *A61M 2039/0273* (2013.01); *A61M 2039/0282* (2013.01)
(58) Field of Classification Search
    CPC ............ A61B 17/0057; A61B 17/0293; A61B 17/3423; A61B 2017/3429; A61F 5/0056
    See application file for complete search history.

(56) References Cited

U.S. PATENT DOCUMENTS

| | | | |
|---|---|---|---|
| 4,850,953 A | | 7/1989 | Haber et al. |
| 5,257,973 A | * | 11/1993 | Villasuso ............... A61B 17/34 128/912 |
| 5,688,247 A | | 11/1997 | Haindl et al. |
| 5,911,706 A | | 6/1999 | Estabrook et al. |
| 5,997,515 A | | 12/1999 | de la Torre et al. |
| 6,083,148 A | | 7/2000 | Williams |
| 6,432,081 B1 | | 8/2002 | Atala |
| 2005/0131325 A1 | | 6/2005 | Chen et al. |
| 2006/0217673 A1 | | 9/2006 | Schulze et al. |
| 2007/0083156 A1 | | 4/2007 | Muto et al. |
| 2007/0088336 A1 | | 4/2007 | Dalton |
| 2007/0161958 A1 | | 7/2007 | Glenn |
| 2008/0021375 A1 | | 1/2008 | Burns et al. |
| 2008/0119798 A1 | | 5/2008 | Chantriaux et al. |
| 2009/0118674 A1 | * | 5/2009 | Patton ............... A61M 39/0247 604/167.02 |
| 2010/0217200 A1 | | 8/2010 | Uth et al. |
| 2010/0312224 A1 | * | 12/2010 | Atthoff ............... A61M 39/1011 604/533 |
| 2011/0218392 A1 | * | 9/2011 | Honaryar ........... A61M 39/0208 600/37 |
| 2015/0182728 A1 | * | 7/2015 | Khalaj ................. A61M 25/02 604/180 |

* cited by examiner

CONICAL PORT

CROSS REFERENCE TO RELATED APPLICATIONS

This application is a 35 U.S.C. § 371 National Phase Entry Application from PCT/AU2011/001204, filed Sep. 19, 2011, and designating the United States, which claims priority under 35 U.S.C. § 119 to Australian Patent Application No. 2010904201 filed Sep. 17, 2010, which is incorporated herein in its entirety.

FIELD OF THE INVENTION

This invention relates to an access port for delivery of fluid to a patient.

The invention has been devised particularly, although not necessarily solely, for delivery of a fluid into, or extraction of a fluid from, a gastric band system for adjusting the gastric band. The invention may, however, have other applications; for example, the invention may have applications in delivery of fluid such as medication or a treatment agent to a patient, or adjustment of a fluid volume in an implant system within a patient.

The patient need not necessarily be human. The patient may, for example, be an animal other than a human, in which case the invention may have veterinary applications.

BACKGROUND ART

The following discussion of the background art is intended to facilitate an understanding of the present invention only. The discussion is not an acknowledgement or admission that any of the material referred to is or was part of the common general knowledge as at the priority date of the application.

Gastric band systems are implanted in patients who typically suffer from obesity. A gastric band system comprises an inflatable band which is implanted around the upper stomach and which is inflated or otherwise adjusted by way of an access port implanted deep to the skin of the patient. The access port includes a catheter which communicates with the gastric band and along which an inflation fluid (such as a saline solution) is conveyed to inflate or otherwise adjust the inflatable band.

Typically, the access port comprises a port body defining a compartment for receiving the inflation fluid. The compartment contains a self-sealing closure which can be penetrated by an adjustment needle through which inflation fluid is delivered or extracted. The closure typically comprises a plug of silicone material. The port body has an outlet which communicates with the compartment and from which a flexible tube extends for communication with the gastric band. The tube provides the catheter. The outlet is provided in the side of the port body such that the catheter extends laterally from the port body. The port body has a flat bottom which rests on the underlying tissue (e.g. muscle/fascia).

Implantation of the gastric band system involves surgical incisions to access the abdominal cavity for installation of the gastric band and an extended surgical incision for installation of the port. The port is typically placed deep to the skin of the patient, being set on muscle/fascia and secured in position by stapling or suturing to the muscle/fascia.

When it is necessary to inflate or otherwise adjust the gastric band, a practitioner (typically a medical practitioner or nurse) locates the port which is set deep to the skin of the patient and inserts the adjustment needle through the skin and into the self-sealing closure of the port to deliver or extract inflation fluid.

While such ports have proved reasonably effective, there are several deficiencies.

One deficiency arises from the positioning of the catheter in relation to the port body. Because the catheter extends laterally from the port body, the catheter is vulnerable to being pierced and damaged by the adjustment needle in the event that the practitioner inadvertently misses the self-sealing closure during attempted insertion of the adjustment needle.

Another deficiency is that the port body, which has a flat bottom, may have a tendency to tilt or shift within the patient after implantation of the port, and even invert when in position, thereby causing difficulties in performing adjustments to the implanted gastric band.

Yet another deficiency is that the part of the port body to which the catheter is connected is rigid, thus creating a point of stress at which the catheter is prone to fracturing.

It is against this background that the present invention has been developed.

Accordingly, it is an object of the present invention to ameliorate one or more of the abovementioned deficiencies, or at least provide an alternative access port.

DISCLOSURE OF THE INVENTION

According to a first aspect of the invention there is provided an access port comprising a port body and a catheter, the port body defining a cavity into which a fluid can be delivered or from which a fluid can be extracted through one side of the port body, the catheter being in communication with the cavity and being disposed on an opposed side of the port body.

Preferably, said one side of the body is adapted to receive an adjustment needle for delivery of the fluid into the cavity.

Preferably, the said one side is adapted for extraction of the fluid through said one side.

Preferably, the port body is adapted to protect the catheter from the adjustment needle, by having the catheter disposed on the side of the port body opposed to that side to which the needle is presented for fluid adjustment.

Preferably, the port body comprises a compartment having a self-sealing portion which can be penetrated by an adjustment needle for delivery of fluid to the cavity or for extraction of fluid from the cavity.

Preferably, the port body comprises an outlet on said opposed side which communicates with the cavity and from which the catheter extends.

Preferably, the opposed side of the body is of resilient construction to provide a flexible connection with the catheter.

Preferably, the opposed side of the body is of resilient construction.

Preferably, the opposed side of the body is configured to at least partly close a hole in the body of a patient.

Preferably, the hole comprises a laparoscopic access hole in the muscle/fascia of the patient.

Preferably, the opposed side of the body is configured as a plug.

Preferably, the opposed side of the body is adapted to close holes of various sizes.

Preferably, the body portion comprises a barrier to limit the depth to which a needle can penetrate into the port.

Preferably, the barrier is positioned within the cavity between said one side of the port body and the opposite side of the port body.

Preferably, the barrier comprises a barrier plate supported in spaced relation with respect to the opposite side of the port body.

Preferably, the barrier plate comprises a plate formed of metal or any other appropriate hard material.

According to a second aspect of the invention there is provided an access port comprising a port body and a catheter, the port body having first and second sides in opposed relation, the first side being adapted to receive an adjustment needle for delivery or extraction of a fluid, and a catheter disposed on the second side to receive and convey the fluid.

According to a third aspect of the invention there is provided an access port comprising a port body, the port body defining a cavity into which a fluid can be delivered or from which a fluid can be extracted through one side of the port body, the body being configured to at least partly close a hole in the body of a patient.

According to a fourth aspect of the invention there is provided an access port comprising a port body, the port body defining a cavity into which a fluid can be delivered or from which a fluid can be extracted through one side of the port body, an outlet communicating with the cavity on an opposed side of the port body, the opposed side of the body being configured to at least partly close a hole in the body of a patient.

According to a fifth aspect of the invention there is provided an access port comprising a port body, the port body defining a cavity into which a fluid can be delivered or from which a fluid can be extracted through one side of the port body, a catheter communicating with the cavity on an opposed side of the port body, the opposed side of the port body being configured to at least partly close a hole in the body of a patient.

Preferably, the hole comprises a laparoscopic access hole in the muscle/fascia of the patient.

According to a sixth aspect of the invention there is provided an access port comprising a port body, the port body defining a cavity into which a fluid can be delivered or from which a fluid can be extracted through one side of the port body, a catheter communicating with the cavity on an opposed side of the port body, the opposed side of the port body being of resilient construction to provide a flexible connection between the port body and the catheter.

According to a seventh aspect of the invention there is provided an access port comprising a port body into which a fluid can be delivered through one side of the port body, a catheter on an opposed side of the port body, wherein the opposed side of the body is configured to at least partly close a hole in the body of a patient, and wherein the opposed side of the port body is of resilient construction to provide a flexible connection between the port body and the catheter.

Preferably, the flexibility of the flexible connection between the port body and the catheter increases progressively in the direction away from the port body Preferably, the opposed side of the port body is of tapered configuration facilitating the progressive increase in flexibility of the connection between the port body and the catheter.

Preferably, the port body is adapted to close holes of various sizes. This is possible because of the tapered configuration of the opposite side of the port.

According to an eighth aspect of the invention there is provided an access port comprising a port body and a catheter, the port body defining a cavity into which a fluid can be delivered or from which a fluid can be extracted through one side of the port body, the catheter being adapted to receive and convey the fluid, the port body comprising integral means for anchoring the port body to the body of the patient.

Preferably, the means for anchoring comprises at least one first resilient member attached to the port body and the at least one first resilient member being adapted to engage at a location in the subcutaneous tissues for anchoring the port body to the body of the patient, Preferably, each of the at least one first resilient members is adapted to be deformed to a contracted condition for delivery of the resilient members to the location in the subcutaneous tissues of the patient.

Preferably, the body is configured to at least partly close a hole in the body of the patient.

Preferably, the access port further comprises at least one second resilient member being adapted to engage at a location in the peritoneal cavity for anchoring the port body to the body of the patient, Preferably, each of the at least one second resilient members is adapted to be deformed to a contracted condition for delivery of the resilient members to the location in the peritoneal cavity of the patient.

Preferably, the port body comprises an opposite side configured to at least partly close the hole, the at least one second resilient member being attached to the opposite side of the port body or to the catheter.

Preferably, the hole comprises a hole in the muscle/fascia of the patient,

Preferably, the port body further comprises a membrane attached to the opposite side of the port body or to the catheter, the membrane being adapted to be collapsed for insertion in the hole of the body of the patient and to be expanded to cover the peritoneal side of the hole. This arrangement is particular useful because it reduces or eliminates the risk of herniation.

Preferably, the membrane comprises a flexible membrane.

Preferably, the membrane seals the hole.

Preferably, the port body further comprises a recoil device attached to the opposite side of the port body for insertion in the hole, the recoil device being adapted for insertion in the hole.

Preferably, the at least one second resilient member is attached to the recoil device.

Preferably, the recoil device is adapted to expand and contract so as to vary the distance between the at least one first resilient member and the at least one second resilient member. This is particularly useful during placement of the port. Also, the dimensions of the recoil device can adjust as the patient's weight change.

According to a ninth aspect of the invention there is provided an applicator for applying an access port to a hole in a body of a patient, the applicator comprising a body for containment of the access port, the body of the applicator comprising a proximal end adapted to receive the access port, and a distal end comprising a resilient conical portion for insertion in the hole in the body of the patient for delivery of the access port into the hole.

Preferably, the proximal end of the applicator comprises at least one handle.

Preferably, the access port is an access port comprising a plurality of resilient members for anchoring the access port to the body of the patient.

Preferably, the body of the applicator is adapted to receive and confine the access port such that the plurality of resilient members are in contracted condition for delivery of the access port to the hole in the body of the patient.

Preferably, the resilient conical portion is adapted for insertion in the hole for delivery of at least one of the plurality of resilient members into the peritoneal cavity of the patient.

Preferably, the applicator is adapted to receive an extractor for delivery to the location of the access port for extraction of the access port.

According to a tenth aspect of the invention there is provided an extractor for extracting an access port from a hole in the body of the patient, the extractor comprising a body having a proximal end and a distal end hingedly attached to the proximal end, the distal end being adapted to be located in a contracted condition for delivery to the hole in the body of the patient and adapted to be expanded for releasably engaging the access port.

Preferably, the proximal end of the extractor comprises at least one handle.

Preferably, the distal end comprises a plurality of barbs for attachment to the access port to allow extraction of the access port by application of a pulling force to the proximal end.

Preferably, the distal end comprises resilient material allowing expansion of the distal end of the extractor for engagement of the barbs to the access port.

Preferably, the body comprises a cage defined by a plurality of transversal and longitudinal struts.

Preferably, the extractor further comprises an expansion system having a centre and a plurality of arms extending outwardly from the centre, the arms being attached to the longitudinal struts to allow expansion of the distal end during expansion of the arms.

Preferably, the arms comprise resilient material.

Preferably, the arms are configured to expand the distal end of the extractor upon application of a pressure to the centre of the expansion system.

According to a eleventh aspect of the invention, there is provided a sheath for delivering an extractor to a hole in a body of a patient, the sheath comprising a body for containment of the extractor, the body of the sheath comprising a proximal end adapted to receive the extractor, and a distal end comprising a resilient conical portion for insertion in the hole in the body of the patient for delivery of the extractor into the hole.

Preferably, the proximal end of the sheath comprises at least one handle.

According to a twelfth aspect of the invention there is provided a method for anchoring an access port to a hole in a body of a patient, the access port having a plurality of resilient members, the method comprising the steps of:
  insertion of the access port in an applicator having a resilient distal conical portion;
  delivery of the applicator including the access port to the hole in the body of the patient;
  insertion of the resilient distal conical portion of the applicator into the hole;
  extrusion of the access port from the applicator for applying the access port to the hole and insertion of at least one resilient member of the access port into the peritoneal cavity of the patient; and
  extraction of the applicator from the body of the patient.

Preferably, the hole comprises a hole in the muscle/fascia.

Preferably, the at least one second resilient member of the access port is inserted into the peritoneal cavity of the patient.

According to a thirteenth aspect of the invention there is provided a method for extracting an access port from a hole in a body of a patient, the method comprising the steps of:
  inserting an extractor into a hollow body;
  delivering the hollow body including the extractor to a location adjacent to the access port;
  expanding at least a portion of the extractor;
  attaching the expanded portion of the extractor to the access port;
  extracting the access port from the hole by applying a pulling force to the extractor for containment of the access port within the hollow body;
  extraction of the hollow body including the extractor and the access port from the body of the patient.

Preferably, expanding comprises the step of inserting an expander into the hollow body and expand the expander for expanding the at least a portion of the hollow body Preferably, the method further comprises the step of collapsing at least one portion of the extractor for securing the access port to the extractor.

Preferably, the hollow body comprises the applicator according to the ninth aspect of the invention or the sheath according to the eleventh aspect of the invention.

Preferably, the method further comprises the step of collapsing a plurality of resilient members of the access port during containment of the access port within the hollow body.

According to a fourteenth aspect of the invention there is provided a stabiliser comprising at least one resilient member having an end being adapted to be attached to a surgical device for anchoring of the surgical device within the body of a patient.

Preferably, the resilient member comprises attachment means for attaching the stabiliser to the surgical device.

Preferably, the resilient member is of curved configuration.

BRIEF DESCRIPTION OF THE DRAWINGS

The invention will be better understood by reference to the following description of four specific embodiments thereof as shown in the accompanying drawings in which.

It should be noted that the figures are schematic only and the location and disposition of the access ports, applicators, extractors and sheaths may vary according to the location and type of surgical procedure performed. Also, it should be noted that all figures are not necessarily to scale.

BEST MODE(S) FOR CARRYING OUT THE INVENTION

Figure 1:
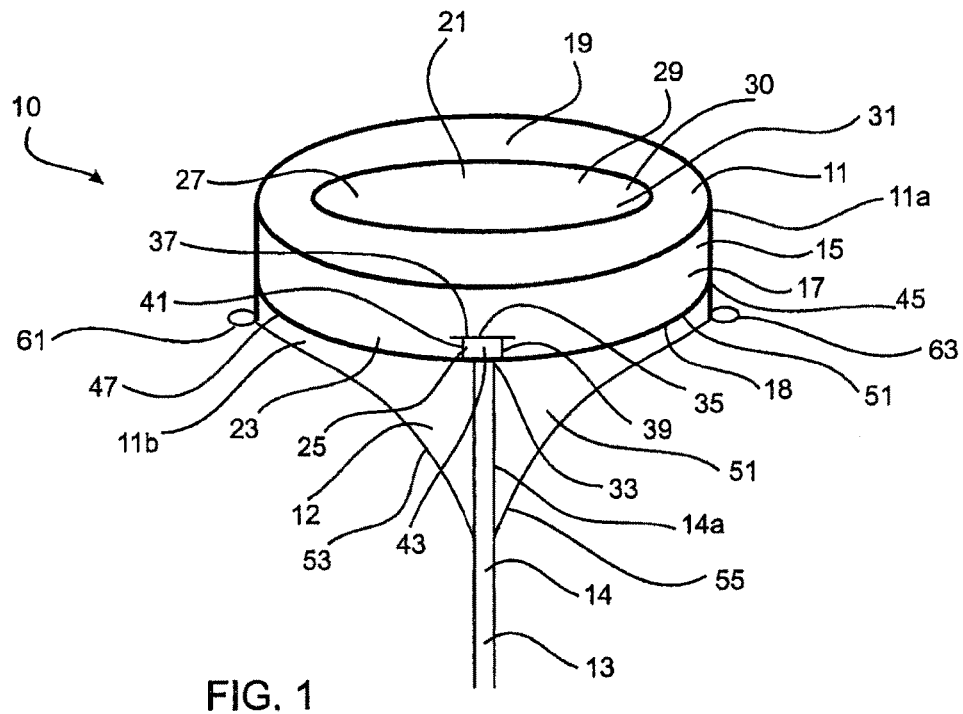
FIG. 1 is a schematic fragmentary perspective view of an access port according to a first embodiment of the invention.

Referring to FIG. 1, the access port 10 according to the first embodiment comprises a port body 11 and a catheter 13. The port body 11 defines an outlet 12 to which the catheter 13 is connected. Only an end section of the catheter 13 is shown in FIG. 1.

The catheter 13 comprises a flexible tube 14.

The port body 11 comprises an upper portion 11a and a lower portion 11b integrally interconnected.

The upper portion 11a comprises a rigid housing 15 defining a peripheral sidewall 17, a base 18 and a top 19 having an access opening 21. The housing 15 defines an interior compartment 23 which is above the base 18 and which incorporates a cavity 25. The opening 21 opens onto the interior compartment 23 and is closed by an insert portion 27 in the form of a plug 29 of material such as silicon which provides a self-sealing closure 30 for the opening 21. With this arrangement, the plug 29 presents an exterior surface 31 to which an adjustment needle (not shown) can be presented, as will be explained in more detail later.

The exterior surface 31 and the catheter 13 are on opposed sides of the body portion 11, as illustrated in FIG. 1.

The base 18 of the housing 15 incorporates a central opening 33 through which the catheter 13 communicates with the cavity 25 at the outlet 12.

A barrier 35 is provided within the interior 23 between the opening 33 and the exterior surface 31. The barrier 35 comprises a barrier plate 37 mounted on a support 39 above the opening 33. The support 39 is configured to permit fluid flow between the interior compartment 23 and the catheter 13. In the arrangement shown, the support 39 comprises a plurality of the legs 41 disposed in circumferential spaced apart relation to define flow passages 43 therebetween. The support 39 determines the distance at which the barrier plate 37 is positioned above the opening 33. This distance can be varied as required during the manufacturing process, according to operating characteristics required of the port 10.

The lower portion 11b of the port body 11 is of resiliently flexible construction and is attached to the underside of the base 18. In this embodiment, the lower portion 11b is formed of an elastic material such as silicone or rubber. The lower portion 11b surrounds the adjacent end section 14a of the flexible tube 14 to provide a flexible connection between the port body 11 and the catheter 13. More particularly, the lower portion 11b provides a flexible connection between the housing 15 and the catheter 13. The flexible connection reduces the likelihood of fracturing of the port 10 at the junction between the port body 11 and the catheter 13.

The lower portion 11b is configured to close, or at least partly close, a laparoscopic access hole in the muscle/fascia of a patient through which hole the catheter 13 extends when the port 10 is implanted in position in the body of the patient, as will be described later. Specifically, the lower portion 11b is configured to define a plug formation 53 for at least partly closing the laparoscopic access hole in the muscle/fascia. In the arrangement shown, the plug formation 53 presents an exterior surface 55 of tapered configuration to facilitate closure of laparoscopic access holes of various sizes in the muscle/fascia of the patients.

Because of the tapered configuration of the resiliently flexible lower portion 11b, the inherent flexibility of the lower portion 11b increases in the downward direction towards the catheter 13. This further enhances the flexibility of the connection between the housing 15 and the catheter 13, thereby further reducing the likelihood of fracturing of the port body 11 or the catheter 13 at or adjacent to the junction between the port body 11 and the catheter 13.

In the typical prior art, the connection between the port body and the catheter is rigid. This rigidity can cause discomfort and can also potentially increase the risk of injury caused by the port to adjacent tissue/organs.

The increasing flexibility of the port 10 in the downward direction reduces the likelihood of discomfort and reduces the risk of injury being caused by the port to the underlying tissue/organs.

The body portion 51 further includes anchoring means 61 which in the arrangement shown comprise eyelets 63 on the housing 15. Other arrangements are, of course, possible; for example, the anchoring means 61 may comprise stapling devices or stabilisers, as described in this document.

In a surgical procedure to implant a gastric band system in a patient, laparoscopic access holes are surgically established in the abdomen of the patient to implant a lap band within the abdominal cavity of the patient in known manner. The port body 11, which is connected to the lap band by way of the catheter 13, is then also implanted. The lower portion 11b of the port body 11 can be so positioned in one of the laparoscopic access holes in the abdomen of the patient that the plug formation 53 at least partly plugs the hole. The tapered configuration of the plug formation 53 accommodates a range of hole sizes.

The lower portion 11b of the port body 11 is embedded into the muscle/fascia tissue at the site of the access hole and may be anchored in position, if considered necessary, by any appropriate means such as stapling, suturing through the eyelets 63 or using stabilisers, as described in this document.

The laparoscopic access hole may be sutured closed about the lower portion 11b of the port body 11, although this may be unnecessary in most circumstances.

It is a feature of the embodiment that the port body 11 is installed at the site of a laparoscopic access, hole. This is advantageous as it avoids the need for a lateral subcutaneous pouch as is required with conventional access ports. This has an associated benefit of a lesser risk of haematoma at the port site because of reduced subcutaneous dissection. Similarly, there is less risk of infection at the site, for the same reason. Further, the port 10 is always located deep to the resultant surgical scar, facilitating location of the port at a later stage. When it is later necessary to access to the port 10 for the purposes of adjusting the lap band, access may be obtained through the scar, which may be less painful for the patient. Still further, in the event that it is later necessary to replace the port 10, less dissection would be required, again reducing the risks of bleeding and infection.

When the lap band requires adjustment, an adjustment needle is passed through or adjacent to the surgical scar and presented to the exterior surface 31. The needle penetrates the self-sealing closure 30 for delivery of the inflation fluid into, or extraction of inflation fluid from, the cavity 25. The barrier 35 limits the extent that the needle can penetrate the body portion 11, and in particular prevents the needle from entering the opening 33. Contact between the needle and the barrier 35 also provides a tangible indication that the needle has encountered the port 10 and penetrated it sufficiently for proper delivery of the inflation fluid. Because the catheter 13 is on the opposed side of the port body 11 to the exterior surface 31, the risk of needle stick damage to the catheter 13 is eliminated or at least much reduced in comparison to the conventional access ports.

It is a further feature of the embodiment that port body 11 is supported in a relatively stable manner within the body of the patient. This is because the lower portion 11b of the port body 11 is embedded into muscle/facia tissue, with the plug formation 53 snugly accommodated in the laparoscopic access hole established during the implant procedure. This reduces the tendency for the port body to tilt or invert in position, which is something that can occur with conventional access ports.

It is a feature of the embodiment that the port body 11 is installed at the site of a laparoscopic access hole. This is advantageous as it avoids the need for a lateral subcutaneous pouch, as is required with conventional access ports. This has an associated benefit of a lesser risk of haematoma or infection at the port site because of reduced subcutaneous dissection.

Figure 2:
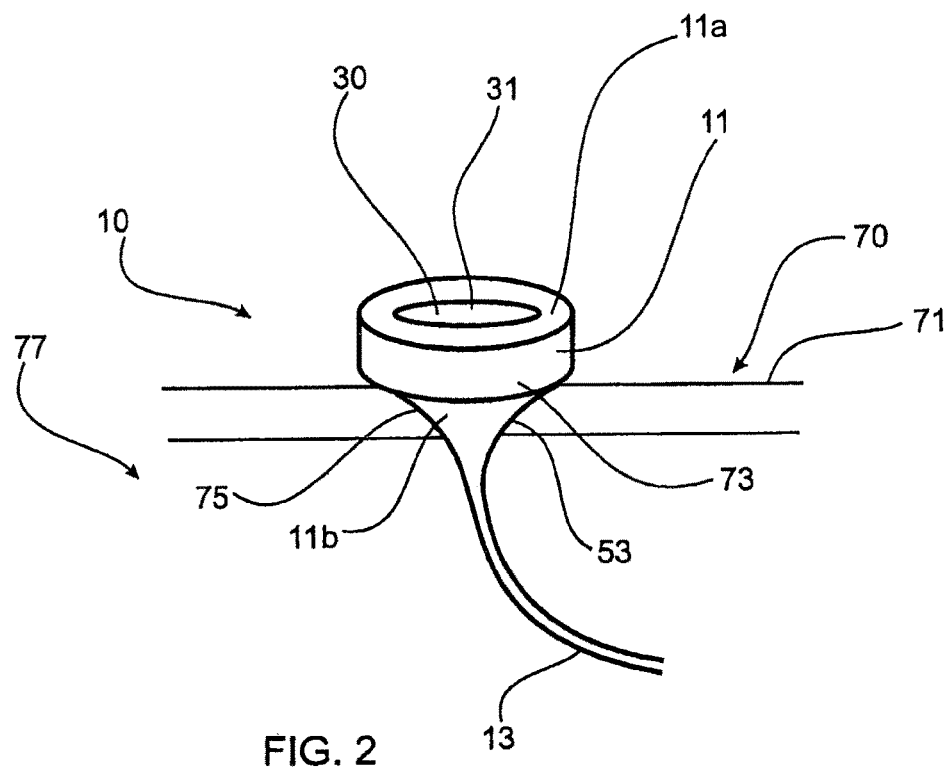
FIG. 2 is a view schematically illustrating the access port according to the first embodiment installed in the body of a patient.

Referring now to FIG. 2, there is shown the port 10 according to the first embodiment installed in the body 70 of a patient. The port 10 is embedded in muscle/fascia 71 in which there is a surgically created tract 73 providing a laparoscopic access hole 75 to the peritoneal cavity 77. As shown, the lower portion 11b plugs the access hole 75 and the catheter 13 extends internally to a lap band (not shown) implanted in the body of the patient. As depicted in FIG. 2, the catheter 13 is disposed on the opposite side of the port body 11 to the self-sealing closure 30 and has an obtuse curve in extending from the port body 11 to the lap band (not shown). Because the port 10 is placed at the site of the laparoscopic access hole 75 opening to the peritoneal cavity 77, and because of the conical shape of the new port, compared with the shape of the conventional port there need only be minimal (if any) extension of the skin and subcutaneous incision (not shown) for placement of the port. Consequently, the skin and subcutaneous incision required for placement of the port 10 can be significantly reduced in comparison to requirements for conventional ports, thus resulting in a smaller wound and a smaller subsequent scar.

Because the curve in the catheter 13 is gentle (obtuse), it does not induce any significantly adverse stress in the port body or the adjacent catheter.

Further, because the access hole 75 is plugged by the lower portion 11b of the port body 11, the catheter 13 is confined and unable to migrate from the peritoneal cavity 77.

Figure 3:
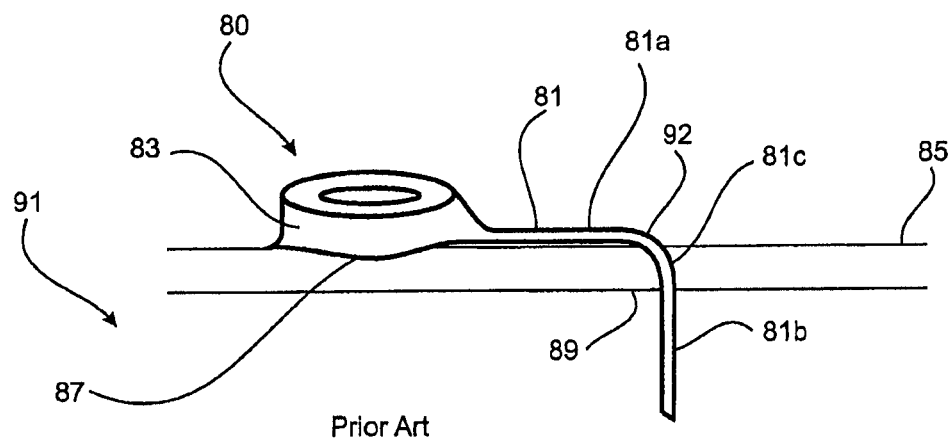
FIG. 3 is a view schematically illustrating a typical prior art access port installed in the body of a patient.

For the purpose of comparison and contrast, FIG. 3 shows a typical prior art port 80 installed in the body of a patient. The prior art port 80 is of conventional construction in which the catheter 81 extends laterally from the port body 83, as previously explained. As depicted in FIG. 3, the port body 83 is set on muscle/fascia 85 at a location 87 adjacent to access hole 89 opening onto the peritoneal cavity 91 of the patient. With this arrangement, the catheter 81 has, in effect, an outer section 81a extending along the muscle 85 to the access hole 89, an inner section 81b disposed within the peritoneal cavity 91, and an intermediate section 81c between the outer and inner sections 81a, 81b. There are various disadvantages with such an arrangement. One disadvantage is that the outer section 81a is exposed on the side of the port body 83, and therefore vulnerable to needle damage. Another disadvantage is that this same section of catheter 81 is at risk of kinking or coiling, thus increasing the risk of catheter fracture at this site. Another disadvantage is that the region between section 81a and intermediate section 81c incorporates an acute bend 92 because of the extent of angulation between the outer and inner sections 81a, 81b. The acute bend 92 creates a region of stress in the catheter 81, particularly with the repetitive muscular movement in this region, which increases the risk of catheter fracture. Another disadvantage is the potential for the inner section 81b of the catheter 81 to migrate from the peritoneal cavity 91 outwardly through the access hole 89. Such migration can cause more of the catheter 81 to be exposed to needle damage and acute angulation. One of the current methods of reducing the risk of catheter migration with conventional ports is to suture the catheter to the muscle/fascia at a location close to the access hole 89. Suturing the catheter 81 in this way requires additional work and time, and also carries its own risk of damage to the catheter 81.

Figure 4:
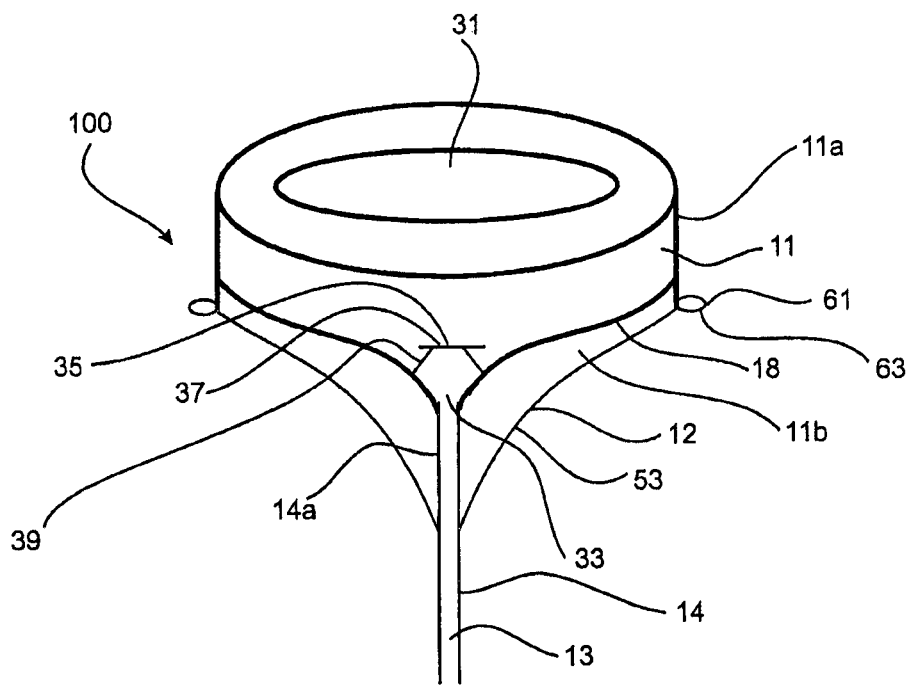
FIG. 4 is a schematic fragmentary perspective view of an access port according to a second embodiment.

Referring now to FIG. 4, there is shown an access port 100 according to a second embodiment. The access port 100 is similar in many respects to the access port 10 and so similar reference numerals are used to identify similar parts. The access port 100 differs from the access port 10 in relation the configuration of the base 18 and the associated opening 33, as well as the barrier 35 and the barrier supports 39.

FIGS. 5 to 10 and 17 show access ports 200 and 300 in accordance with third and fourth embodiments of the invention. The access port 200 and 300 differs from the access ports 10 and 100 in that the access port 200 and 300 include integral anchoring means. The use of integral anchoring means for anchoring the access port 200 and 300 is particularly advantageous because is allows securing the access ports 200 and 300 in position in the body without the need for a separate securing means such a suture or stapling. As will be described in the following description, the integral anchoring means comprise stabilisers 210 that secure the access port 200 and 300 within the access hole 89. Using the stabilisers 210 for securing the access port 200 and 300 to the access hole 89 is particularly advantageous because it avoids the use of attachment means 61 based on stitching or stapling for fastening of the access port 200 and 300 to the muscle/fascia 212.

The stabilisers 210 may be an integral part of the access ports 200 and 300. Alternatively, the stabilisers 210 may be attached to the access ports 200 and 300 prior implanting the access ports 200 and 300. For this there are provided at the stabilisers and/or the access ports attachments means for attachment of the stabilisers 210 to the access ports 200 and 300.

Figure 5:
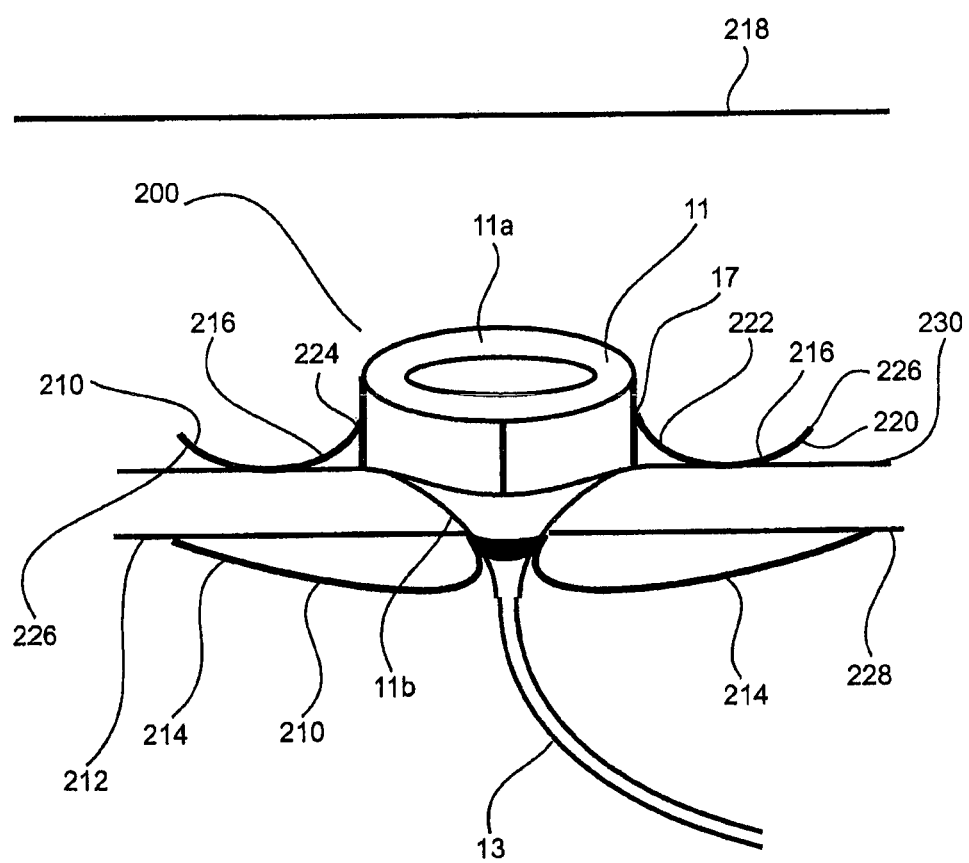
FIG. 5 is a schematic fragmentary perspective view of a second arrangement of the access port according to a third embodiment of the invention.

Further, FIG. 5 shows an access port 200 according to a third embodiment of the invention. The access port 200 is similar in many respects to the access ports 10 and 100 so similar reference numerals are used to identify similar parts.

The access port 200 comprises inner stabilisers 214 and outer stabilisers 216. The inner stabilisers 214 are located below the muscle/fascia within the abdominal cavity. Thus, the inner stabilisers 214 may also be referred to as intra-peritoneal stabilisers. The outer stabilisers 216 are located below the skin 218 superficial to the muscle/fascia 212. The outer stabilisers 216 may also be referred to as subcutaneous stabilisers.

The stabilisers 210 extend radially outward from the access port 200. The stabilisers 210 surround the periphery side wall 17 of the access port 200 and are located at spaced apart locations with respect to each other. In the arrangement shown there are four outer stabilisers 216 and four inner stabilisers 214 (see FIGS. 8 and 9). In the arrangement of the third embodiment of the invention, the inner and outer stabilisers 210 are directly attached to the port body 11. As shown in FIG. 5, the inner stabilisers 214 are attached to the lower portion 11*b* of the port body 11; the outer stabilisers 216 are attached to the peripheral sidewall 17 of the port body 11. In an alternate arrangement, the inner stabilisers 214 may be attached to the catheter 13 (see FIG. 17)

The outer stabilisers 216 extend outwardly from the periphery side wall 17 of the access port 200. The outer stabilisers 216 are curved. Thus, each outer stabiliser 216 has a concave surface 222 and a convex surface 220. A first end 224 of each outer stabiliser 216 is attached to the peripheral sidewall 17 of the access port 200. The second end 226 is a free end located distal to the sidewall 17. The outer stabilisers 216 are attached to the access port 200 such that the convex surface 220 of the outer stabilisers 216 faces the patient's muscle/fascia when the access port 200 is secured in the access hole 89.

The inner stabilisers 214 are attached to the lower portion 11*b* of the access port 200. The inner stabilisers 214 are also curved. As will be described at a later stage, there are two different arrangements of access ports 200. In a first arrangement, the inner stabilisers 214 are attached to lower portion 11*b* of the access port 200 such that the convex surface 220 of the stabilisers 214 faces the inner side 228 of the muscle/fascia 212 onto which the access port 200 is attached (see FIG. 17). In the second arrangement, the concave surface 222 of the stabilisers 214 faces the inner side 228 of the muscle/fascia 212 (see FIG. 5).

The stabilisers 210 are of resiliently flexible construction. This allows the stabilisers 210 to be resiliently deformed from a normal condition to a collapsed condition (see FIGS. 11 to 14). This is particularly useful for applying the access port 200 on the access hole 89.

Because, of their resiliently flexible construction, the stabilisers 210 when collapsed will have an inherent tendency to return to their normal condition. This tendency to return to the normal condition provides a reactive force opposite to the force being applied to the stabilisers 210 when they are deformed. As will become evident when describing the method for applying the access port 200 to the access hole 89, this tendency of the stabiliser to return to its normal condition is particular advantageous for applying of the access port 200 on the access hole 89.

Figure 12:
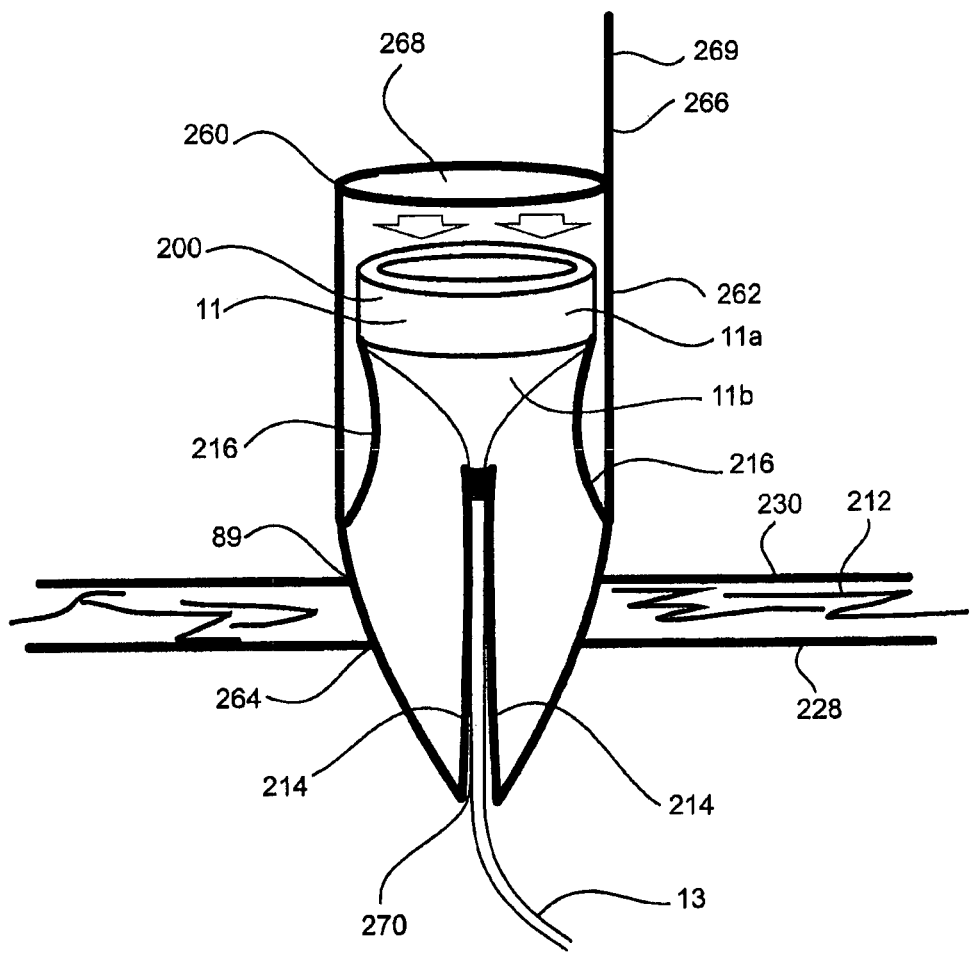
FIG. 12 is a schematic fragmentary perspective view of a second arrangement of the access port according to the third embodiment of the invention during mounting to a patient's muscle/fascia.

Also, the fact that the stabilisers 210 have an inherent tendency to return to their normal condition secures the access port 200 to the access hole 89. Referring, for example, to FIG. 5 and FIG. 12, as the access port 200 is being mounted on the access hole 89, the outer stabilisers 216 as well as the inner stabilisers 214 are displaced from their normal condition. Because, the stabilisers have been deformed, reactive forces (generated in view of the tendency of the stabilisers 210 to return to their normal condition) are applied to deploy the stabilisers into their desired positions. In this manner, the inner and outer stabilisers are engaged, respectively, at a location in the peritoneal cavity and at a location in the subcutaneous tissues. The outer stabilisers 216 act as a brake means to prevent inward migration of the access port. The inner stabilisers 214 act as a hook means to prevent outward migration of the access port. Accordingly, there is no need for suturing or stapling of the access port 200 to the muscle/fascia 212.

Figure 8:
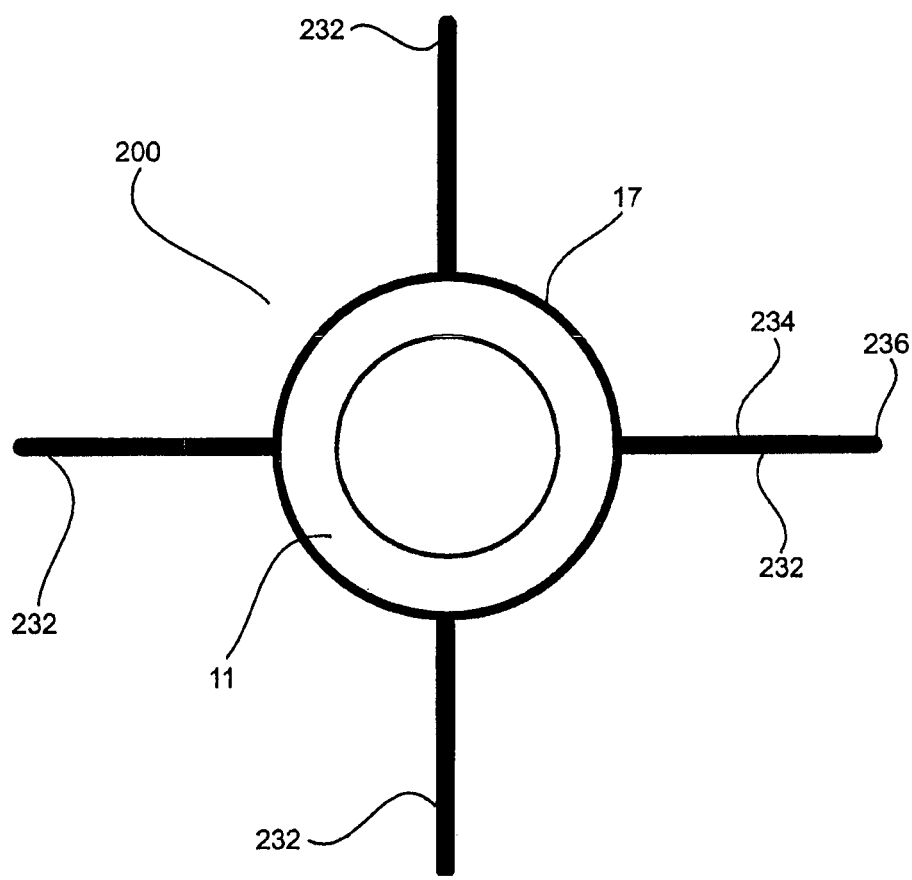
FIG. 8 is a schematic top view any of the access port according to the third or fourth embodiments of the invention
Figure 9:
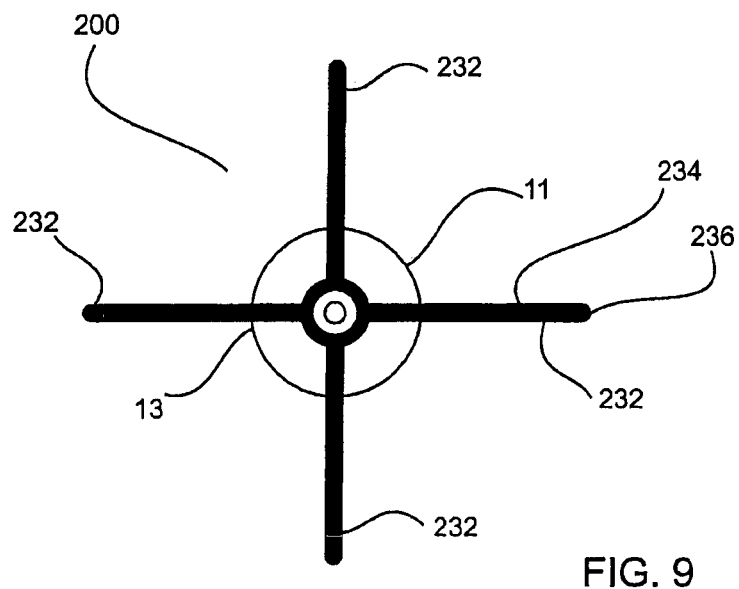
FIG. 9 is a schematic bottom view of the access ports shown in any of FIGS. 5 to 7 and FIG. 17.
Figure 10:
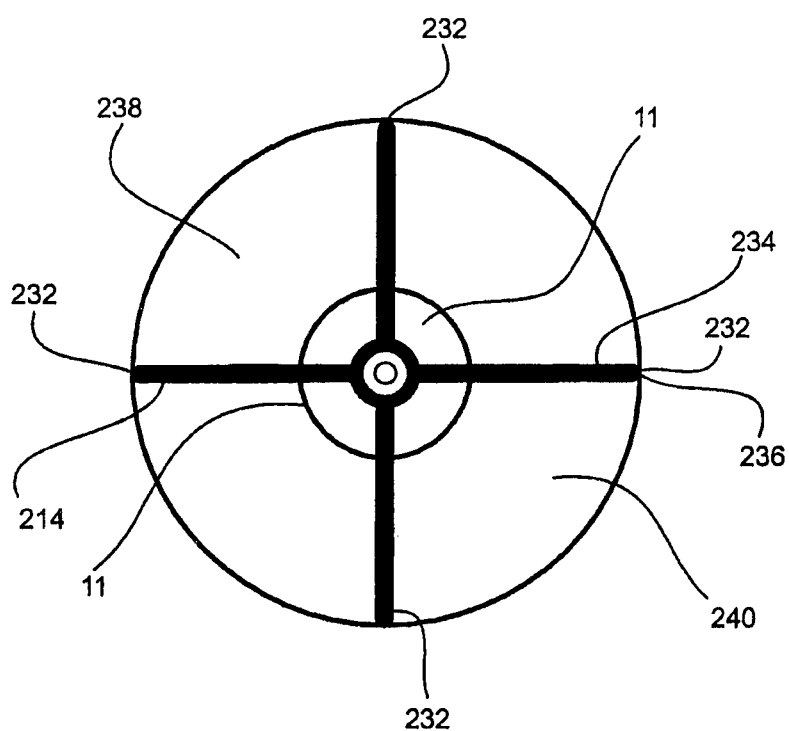
FIG. 10 is schematic bottom view of another arrangement (including the flange) of the access ports shown in any of FIGS. 5 to 7 and FIG. 17.

Referring now to FIGS. 8 to 10, the stabilisers comprise resilient members 232 having blunted edges 234 and blunted tips 236. The blunted edges 234 and tips 236 reduces tissue trauma during applying of the access port 200 on the patient's muscle/fascia 212. The resilient members 232 may be of any resilient material, such as plastic or metal, among others.

Further, a membrane 238 may be attached to the access port 200. The membrane 238 fills the gaps between the inner stabilisers 214 and is attached to the inner stabilisers (in a fashion similar to the attachment of the material to the spokes in an umbrella) of the access port 200 defining a flange 240. (see FIG. 10). When the access port 200 is attached to the muscle/fascia 212, the membrane 238 lies close to the inner side 228 of the muscle/fascia 212. In this manner, the membrane closes the access hole 89 in which the port is located defining a barrier. In an arrangement, the membrane may seal the access hole so as to prevent herniation of intra-peritoneal contents through the access hole 89

The membrane 238 comprises flexible material. With this arrangement, the membrane 238 can be collapsed in order to insert the membrane 238 together with the inner stabilisers 214 into the abdominal cavity. After insertion of the collapsed membrane 238, the membrane returns to its expanded condition because of the resilient construction of the inner stabilisers. The membrane 238 may be of any flexible and non adhesion forming material, such as silicone, among others.

Figure 6:
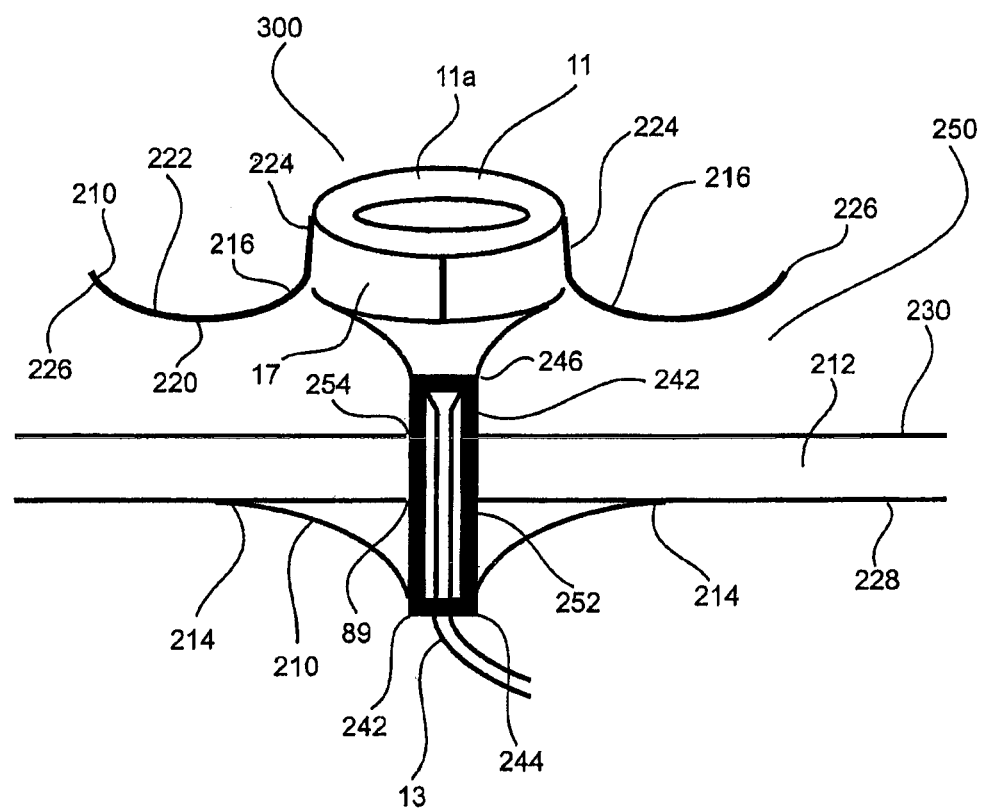
FIG. 6 is a schematic fragmentary perspective view of an access port according to a fourth embodiment of the invention.
Figure 7:
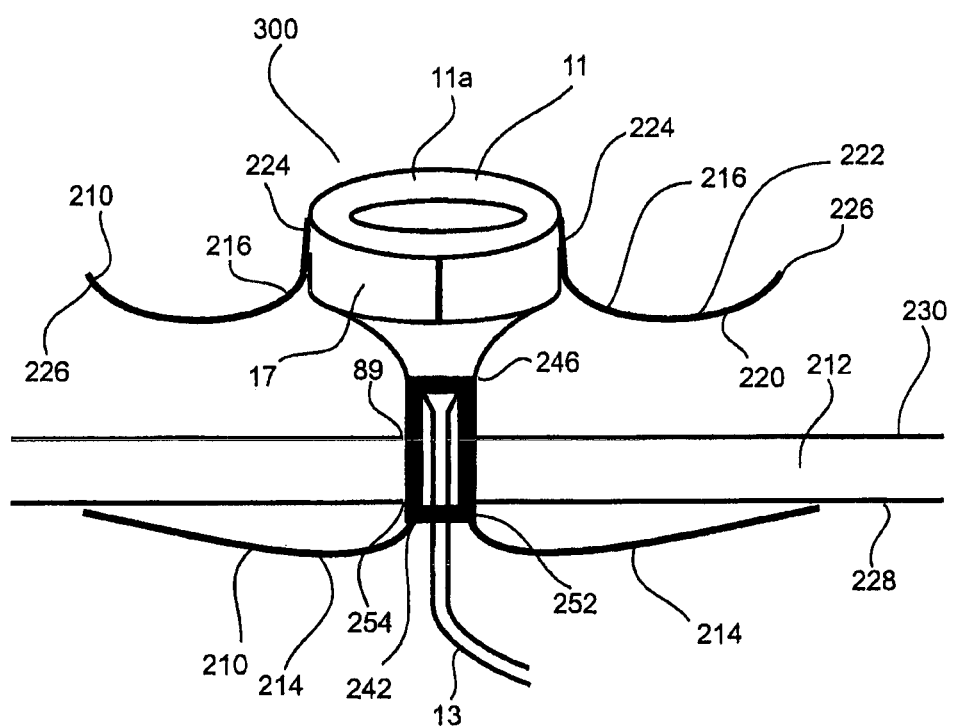
FIG. 7 is a schematic fragmentary perspective view of an access port according to a second arrangement of the fourth embodiment of the invention.

Further, FIGS. 6 and 7 shows an access port 300 according to a fourth embodiment. The access port 300 is similar in many respects to the access port 200 so similar reference numerals are used to identify similar parts.

The access port 300 differs from the access port 200 in that it includes a recoil device 242. In the arrangement of the fourth embodiment of the invention, the outer stabiliser 216 is directly attached to the access port 300 and the inner stabiliser 214 and the membrane 238 (if present) are indirectly attached to the access port 300. As shown in FIG. 6, the outer stabiliser 216 is attached to the sidewall 17 of the port body 11 and the inner stabiliser 214 is attached to the recoil device 242.

FIG. 6 shows an access port 300 having the recoil device 242. The recoil device 242 maintains the access port 300 and the inner stabilisers 214 together. The recoil device 242 has a distal end 244 and a proximal end 246. The proximal end 246 is attached to the lower portion 11b of the access port 300. The inner stabilisers 214 are attached to the distal end 244 of the recoil device 242. The recoil device 242 is adapted to receive the catheter 13. This allows the catheter 13 to extend from the lower portion 11b of the access port and through the recoil device 242 for insertion into the access hole during application of the access port 300 on the muscle/fascia 212 or into the subcutaneous tissue.

The recoil device 242 comprises resilient material. This means that the recoil device 242 may be deformed by application of a force. Once the force is removed, the recoil device 242 returns to its normal condition. The normal condition of the recoil device 242 is the contracted condition. As was previously described with reference to the stabilisers 210, the tendency of the recoil device 242 to return to its normal condition provides a reactive force which opposes the force generated as the recoil device 242 is expanded from its contracted condition. It is this force which secures the access port 300 to the access hole 89 or within the subcutaneous tissue.

The access port 300 is particularly useful in cases where it is desired to position the access port 300 at different distances from the muscle/fascia of the abdominal wall. The access port 300 can be located at different distance from the muscle/fascia 212 because the recoil device 242 can be expanded up to a maximum size. In an arrangement where the recoil device is being used, the access port 300 may only cover at least partially the hole as the access port 300 may be situated some distance superficial to the hole.

Also, the access port 300 is capable of automatic adjustment as the patient experiences weight changes.

For example, as shown in FIG. 6, the access port 300 may be located on a layer of fat 250 lying on the exterior side 230 of the muscle/fascia 212. If the patient loses weight and the thickness of the layer of fat 250 is reduced, the length of the recoil device 242 is also reduced. This is because, as mentioned before, the recoil device 242 has a tendency to return to its normal condition. Reducing the length of the recoil device 242 maintains tension between the inner and outer stabiliser 214 and 216, respectively. This keeps the access port 300 secured on the access hole 89 or in the subcutaneous tissue in a relatively stabilised fashion, facing the skin.

The recoil device 242 may comprise a cylindrical body 252 comprising resilient material. Alternatively, the recoil device 242 may comprise a spring such as a helical spring. Other arrangements may include magnets.

Figure 11:
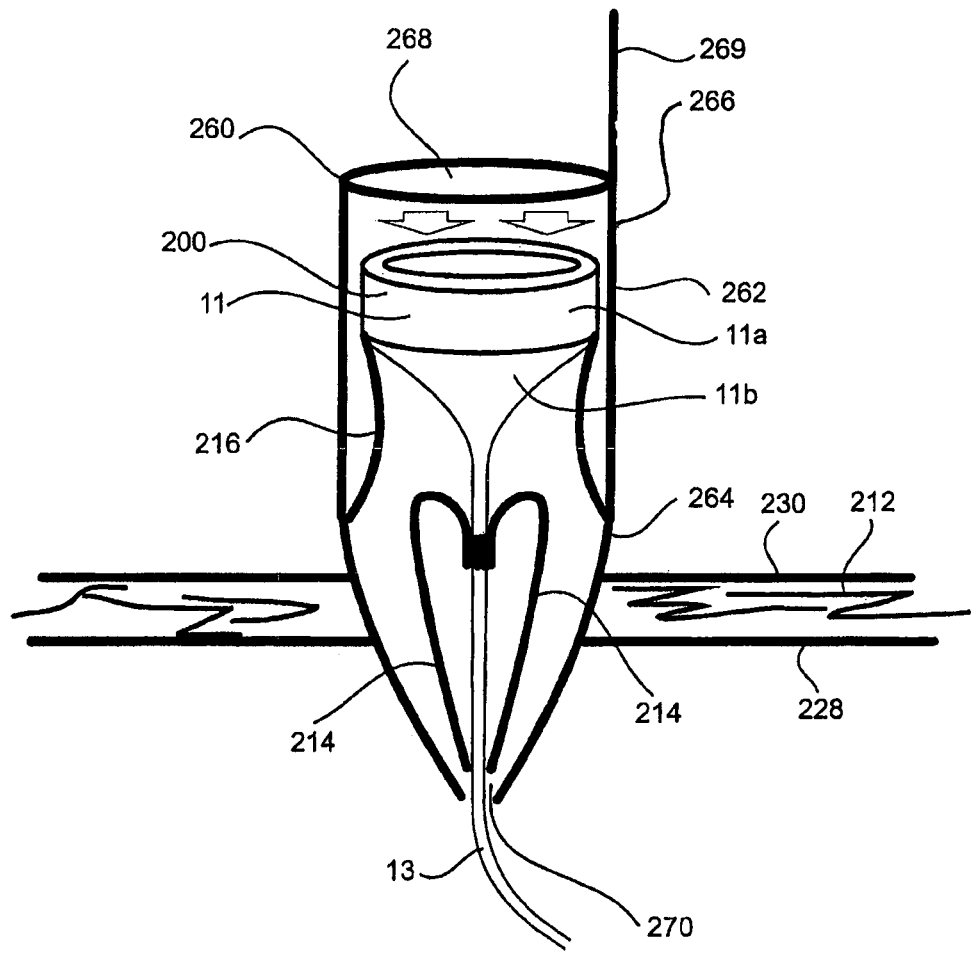
FIG. 11 is a schematic fragmentary perspective view of a first arrangement of the access port according to the third embodiment of the invention during mounting to a patient's muscle/fascia.
Figure 13:
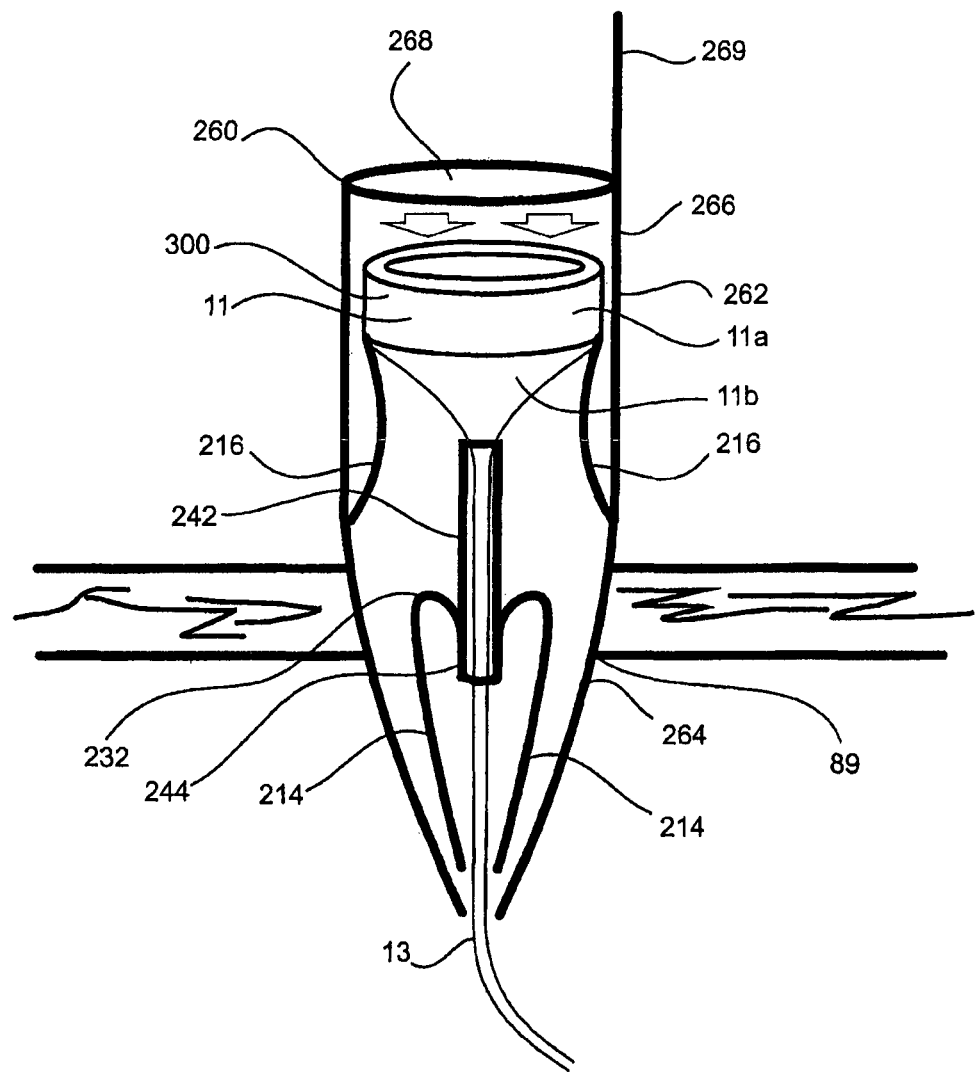
FIG. 13 is a schematic fragmentary perspective view of the first arrangement of the access port according to the fourth embodiment of the invention during mounting to a patient's muscle/fascia.
Figure 14:
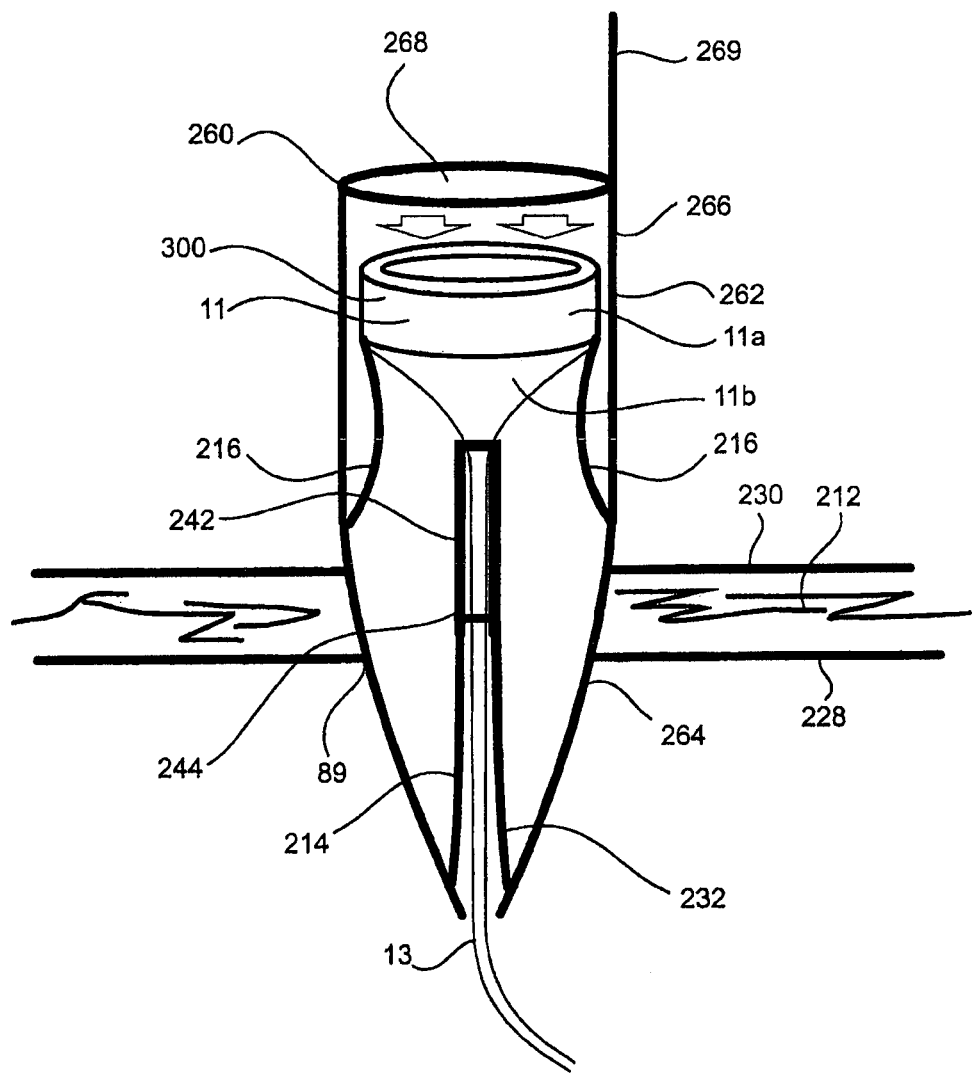
FIG. 14 is a schematic fragmentary perspective view of the second arrangement of the access port according to the fourth embodiment of the invention during mounting to a patient's muscle/fascia.

Referring now to FIGS. 11 to 14, there are two arrangements for each of the access port 200 and access port 300. FIGS. 11 and 13 show a first arrangement of the access ports 200 and 300, respectively. FIGS. 12 and 14 show a second arrangement of the access ports 200 and 300, respectively. The first arrangement differs from the second arrangement in the manner in which the inner stabilisers 214 are positioned in their normal condition and in their deformed condition.

Figure 17:
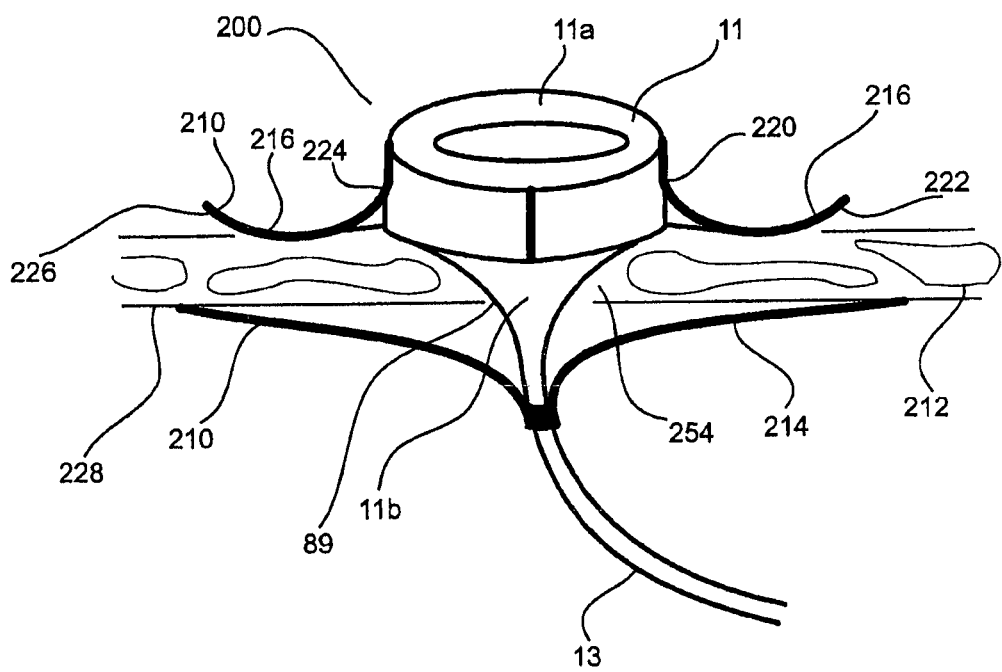

In accordance with the first arrangement of the access ports 200 and 300, the inner stabiliser 214 is attached to the lower portion 11b of the access port 200 and/or the catheter 13 (or in the case of the access port 300, to the distal end 244 of the recoil device 242) such that the resilient, members 232 of each of the stabilisers 214, in their normal condition, extend convexly towards the access port 200 (or 300). In this arrangement, the stabilisers 214 are positioned in the deformed condition by folding the resilient members 232 over themselves. FIG. 11 shows the first arrangement of the access port 200 as it is mounted on the access hole 89. FIG. 17 shows the first arrangement of the access port 200 after having been mounted on the access hole 89.

In accordance with the second arrangement of the access ports 200 and 300, the inner stabiliser 214 is attached to the lower portion 11b of the access port 200 and/or the adjacent catheter 13 (or in the case of the access port 300, the distal end 244 of the recoil device 242) such that the resilient members 232 of each stabilisers 214, in their deformed condition, extend opposite to the access port 200 or 300. In this arrangement, the normal condition of the stabilisers 214 is such where the resilient members 232 extend concavely towards the access port 200 or 300. FIG. 12 shows the second arrangement of the access port 200 as it is mounted on the access hole 89. FIG. 5 shows the second arrangement of the access port 200 after having been mounted on the access hole 89.

As mentioned before, any of the access ports in accordance with the first to fourth embodiment of the invention may be adapted to be mounted on the access hole 89. The following descriptions of the methods for applying and removing the access port will be made with reference to the access port 200 in accordance with the third embodiment of the invention. However, the methods for applying and removing the access port 200 can be applied to any of the access ports in accordance to the first to fourth embodiment of the invention. Also, the methods can be used for other type of ports or other implanted devices used during gastric band surgical procedures and other procedures.

Initially, an incision is made in the patient's body. The incision is made such that it extends from the upper surface of the patient's skin to the muscle/fascia wall of the abdominal cavity. After making the incision, the muscle/fascia abdominal wall is punctured in order to form the access hole 89 for insertion of the lower portion 11b of the access port 200.

Once the incision and the access hole 89 have been made, the access port 200 is inserted into the incision and delivered to the access hole 89. At this stage the lower portion 11b of the access port 200 is inserted in the access hole 89. In order to insert the access port 200 into the incision and the lower portion 11b into the access hole 89, the outer and inner stabilisers 216 and 214, respectively, must be retracted to their deformed condition. Placing the stabilisers 210 into the deformed condition facilitates delivery of the access port 200 to the access hole 89 as well as insertion of the inner stabilisers 214 into the peritoneal cavity. Also, in the arrangements of the access port 200 which include the membrane 238 (see FIG. 10), the membrane 238 must also be collapsed for insertion into the abdominal cavity.

By inserting the lower portion 11b of the access port 200 inside the access hole 89, the inner stabilisers 214 are positioned deep to the muscle/fascia 212 which surrounds the access hole 89.

The access port 200 may be applied to the access hole 89 with the aid of an applicator 260. The applicator 260 is adapted to contain the access port 200 such that the stabilisers 210 are forced into the deformed condition. This facilitates insertion of the access port into the incision and delivery to the access hole 89. Also, insertion of the inner stabilisers 214 within the peritoneal cavity is facilitated because the inner stabilisers 214 are kept in the deformed condition during insertion of the lower portion 11b of the access port 200.

As mentioned before, the inner and outer stabilisers 214 and 216, respectively, have the tendency to return to their normal condition when the force maintaining the stabilisers 210 in deformed condition is released. This means that when the inner and outer stabilisers 214 and 216, respectively, exit the applicator 260, the stabilisers 214 and 216 return to their normal condition as shown in FIGS. 5 to 7 and FIG. 17. This secures the access port 200 on the access hole 89.

The applicator 260 comprises a cylindrical portion 262 and a conical portion 264 (see FIG. 11). The dimensions of the cylindrical portion 262 and the conical portion 264 are such that the inner and outer stabilisers 214 and 216, respectively, of the access port 200 are collapsed to the deformed condition when the access port 200 is positioned within the applicator 260.

The cylindrical portion 262 comprises an open end 268 and a handle 269. The open end 268 is adapted to receive the access port 200. The conical portion 264 comprises an open end 270 to allow exit of the access port 200 during insertion of the lower portion 11b of the access port into the access hole 89.

The cylindrical portion 262 and the conical portion 264 are integrally connected to define the applicator 260. The cylindrical portion 262 comprises a rigid cylinder 266. The rigid cylinder 266 may be of any material such as metal, plastic, among others.

The conical portion 264 facilitates insertion of the applicator 260 into the access hole 89. The conical portion 264 is made out of resilient material. This allows expansion of the conical portion 264 in order to facilitate exiting of the access port 200.

FIGS. 11 to 14 show the method for applying the access port 200 and 300 to the access hole 89 or applying the access port 300 to the subcutaneous tissue (in the case of access port 300).

In particular, FIGS. 11 and 12 show the application of the first and second arrangements, respectively, of the access port 200 in accordance with the third embodiment. And, FIGS. 13 and 14 show the application of the first and second arrangements, respectively, of the access port 300 in accordance with the fourth embodiment.

Referring to FIG. 11, initially the access port 200 together with the catheter 13 are inserted into the applicator 260. This may be done through the open end 268 of the cylindrical portion 262. Alternatively, the access port 200 may be inserted into the applicator 260 through the open end 270 of the applicator 260.

The access port 200 is located within the applicator 260 such that the catheter 13 extends out from the open end 270 of the conical portion 264. In this way, the catheter 13 can guide the conical portion 264 through the incision and into the access hole 89.

Subsequently, the applicator 260 is inserted into the patient's body. Prior to this however the catheter 13 will already have been connected to the gastric band catheter. Catheter 13 is then inserted in the patient's body followed by the applicator 260. As mentioned before, the catheter 13 guides the applicator 260 into the incision and the access hole 89. Also, tension from the inside of the peritoneal cavity can be applied to the catheter 13 by using an intra-peritoneal grasper to assist the positioning the conical end of the applicator 260 into the access hole 89.

Once the conical portion 264 is located within the access hole 89, the access port 200 can be applied on the access hole 89. This can be accomplished by applying a pressure to the upper portion 11a of the access port 200. The pressure applied to the upper portion 11a of the access port 200 may be applied by a piston or the surgeon's finger. Simultaneously, the conical portion 264 of the applicator 260 may be extracted from the access hole 89 by applying a pulling force to the handle 269 of the applicator 260.

As shown in FIG. 11, by applying the pressure, the access port 200 is pushed through the conical portion 264 of the applicator 260 such that the inner stabilisers 214 are positioned deep to the muscle/fascia 212 which surrounds the access hole 89. Simultaneously, the applicator 260 is withdrawn by applying a pulling force to the handle 269. At this stage the inner stabilisers 214 are located in a condition such that the stabilisers 214 are within the peritoneal cavity and are in contact with or are close to the innerside 228 of the muscle/fascia 212.

After the access port 200 has separated from the applicator 260, the outer stabilisers 216 are displaced from the contracted condition to a condition in which the outer stabilisers 216 are in close proximity to the outer side 230 of the muscle/fascia 212.

Once deployed within the body, the inner and outer stabilisers 214 and 216, respectively, sandwich the muscle/fascia 212. In this manner, the access port 200 is secured to the access hole 89, as previously described.

At this stage, the applicator may be extracted from the incision.

Figure 15:
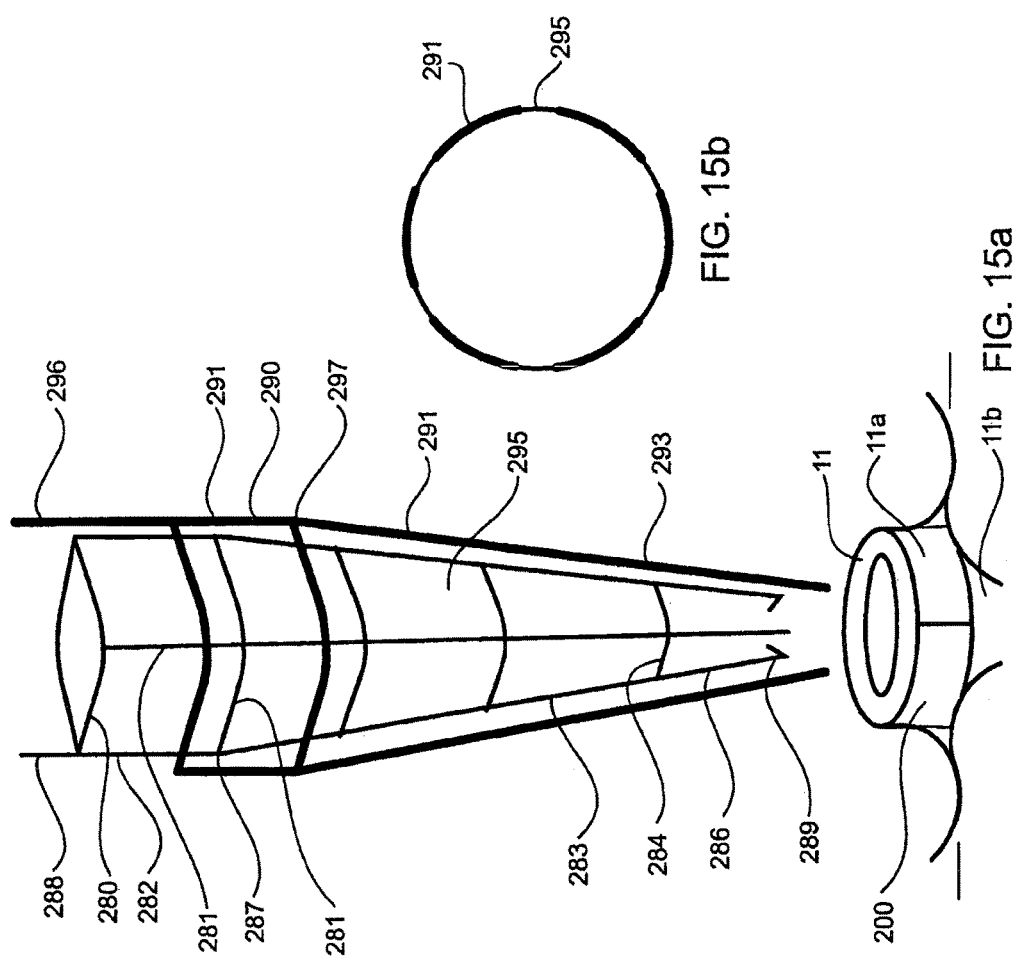
FIG. 15a is a schematic fragmentary perspective view of any of the first to fourth embodiments of the invention prior to dismounting from a patient's muscle/fascia using the first arrangement of an extractor.
FIG. 15b is a cross sectional view of the distal end of the sheath shown in FIG. 15a FIG. 16a is a schematic fragmentary perspective view of any of the first to fourth embodiments of the invention during dismounting from a patient's muscle/fascia using the first arrangement of the extractor.

Moreover, on occasions the access port 200 or 300 may need to be replaced or removed. Removal of the access port 200 or 300 may be performed by using an extractor 280 as shown in FIG. 15 and in FIG. 16.

The extractor 280 comprises a proximal rigid cylindrical body 282 and a distal expandable body 286. The proximal rigid body 282 is defined by a plurality of rigid longitudinal and rigid transversal struts 281. The struts 281 are attached to each other such as to define a cage like structure. The distal expandable body 286 is defined by a plurality of rigid longitudinal struts 283 and a plurality of expandable transverse struts 284.

A handle 288 is attached to the proximal rigid cylindrical body 282. The distal end of the expandable body 286 comprises a plurality of barbs 289. As will be described with reference to the method for extracting the access port 200 or 300, the barbs 289 are adapted to grab the access port 200 or 300.

The extractor 280 comprises resilient material such as plastic or metal, among others.

The distal expandable body 286 is hingedly attached to the proximal rigid body 282. The fact that the transverse struts 284 in the distal expandable body 286 are expandable and that the distal expandable body 286 and the proximal rigid body 282 are hingedly connected, allows the distal body 286 of the extractor 280 to be expanded from a contracted condition (see FIG. 15) to an expanded condition (see FIG. 16). In the expanded condition, the distal expandable body 286 of the extractor 280 has a greater diameter than when the distal expandable body 286 is in the contracted condition. As will be described with reference to the method for extracting the access ports 200 or 300, the fact that the diameter of the distal expandable body 286 of the extractor 280 can be varied facilitates grasping of the access port 200 or 300 by the extractor 280.

The diameter of the distal expandable body 286 may be expanded using an expander, such as, an inflatable expander. Also, a piston may used to increase the diameter of the distal expandable body 286.

Further, extraction of the access port 200 or 300 from the access hole 89 is performed using a sheath 290 adapted to allow the extractor 280 (see FIG. 16) to slide into it. Alternatively, the applicator 260 (used for applying the access port 200 or 300 to the access hole 89) may be used as a sheath for extraction of the access port 200 or 300.

The sheath 290 comprises a rigid proximal cylindrical body 294 and a distal expandable body 293 and a handle 296 attached to the rigid proximal cylindrical body 294. The handle 296 allows manipulation of the sheath 290 into and out of the incision.

The distal expandable body 293 comprises rigid longitudinal struts 291 with intervening elastic material 295. The distal expandable body 293 is hingedly attached to the proximal rigid body 294. The fact that the elastic material 295 between each longitudinal strut in the distal body is expandable and that the distal expandable body 293 is hingedly attached to the proximal rigid body 294 allows the expandable distal body 293 of the sheath 290 to be expanded from a contracted condition (see FIG. 15) to an expanded condition (see FIG. 16). In the expanded condition, the distal expandable body 293 of the sheath 290 has a greater diameter than when the distal expandable body 293 is in the contracted condition. As will be described with reference to the method for extracting the access port 200 or 300, the fact that the diameter of the distal expandable body 293 of the sheath 290 can be varied facilitates the introduction of the extractor 280 down the sheath 290 and into position to allow grasping of the access port 200 or 300 by the extractor 280.

The sheath 290 is adapted to receive the extractor 280 and the access port 200 or 300. As will be described with reference to the method for extracting the port, the extractor 280 is slid into the sheath 290 prior extraction of the access port 200 or 300. During extraction of the access port 200 or 300, the access port 200 or 300 (together with the stabilisers 210 and membrane 238, if the membrane 238 is included) is drawn into the sheath 290. The sheath 290 restrains the stabilisers 210 and membrane 238 (if the membrane 238 is included) from returning to their normal position during extraction of the access port 200 or 300. This facilitates extraction of the extractor 280 and the access port 200 or 300. The sheath 290 may be of any material such as plastic, among others.

Figure 16:
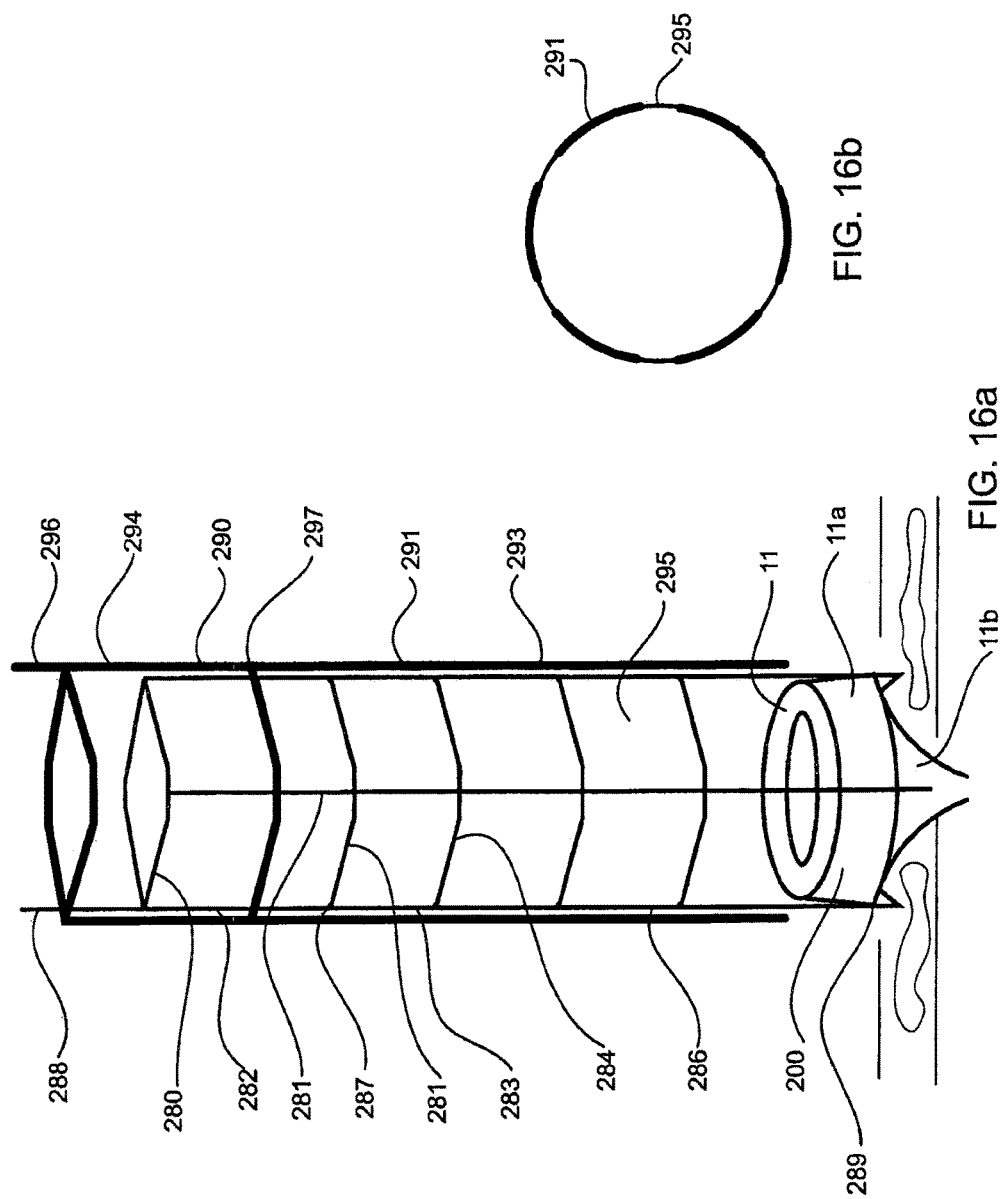
FIG. 16b is a cross sectional view of the distal end of the sheath shown in FIG. 16a FIG. 17 is a schematic fragmentary perspective view of a first arrangement of the access port according to the third embodiment of the invention.

The method for removing the access ports 200 or 300 is shown in FIGS. 15 and 16.

Initially, an incision is made in the patient's body. The incision may be at the location where the incision was previously made during placement of the access port 200 or 300 which now will be removed or replaced. The depth of the incision must be such as to provide access to the access port 200 or 300 to be removed.

After the incision has been made, the extractor 280 is located superficial to the access, port 200 or 300. This is accomplished by inserting the extractor 280 into the sheath 290. The sheath 290, including the extractor 280, is introduced into the incision and delivered to the access port 200 or 300.

The distal expandable bodies 286 and 293 of the extractor 280 and the sheath 290, respectively, are expanded while the extractor 280 and sheath 290 are located superficial to the access port 200 or 300. In the expanded condition, the extractor 280 is mounted on the access port 200 or 300 allowing attachment of the barbs 289 to the lower portion 11b of the access port 200 or 300 (see FIG. 16). After attaching the barbs to the lower portion 11b the diameter of the distal expandable bodies 286 and 293 of the extractor 280 and the sheath 290, respectively, may be reduced in order that the barbs 289 are secured to the access port 200 or 300. In this manner, the extractor 280 is releasable attached to the access port 200 or 300. The diameter of the distal expandable bodies 286 and 293 of the extractor 280 and the sheath 290, respectively, are reduced by, for example, deflating the expander or retracting the piston. The distal expandable body 293 of the sheath 290 which is covering the distal expandable body 286 of the extractor 280 will expand and contract synchronously with the expansion and contraction of the distal expandable body 286 of the extractor 280.

At this stage, the access port 200 or 300 can be extracted from the access hole 89. This is accomplished by pulling the extractor 280 in order to draw the access port 200 or 300 (together with the stabilisers 210 and membrane 238, if the membrane 238 is included) further into the sheath 290. Once the access port 200 or 300 (together with the stabilisers 210 and membrane 238, if the membrane 238 is included) is contained within the sheath 290, the sheath 290 may be extracted from the patient's body by pulling the handle 296 of the sheath 290 in order to retrieve the sheath 290 including the access port 200 or 300 and the extractor 280.

Figure 18:
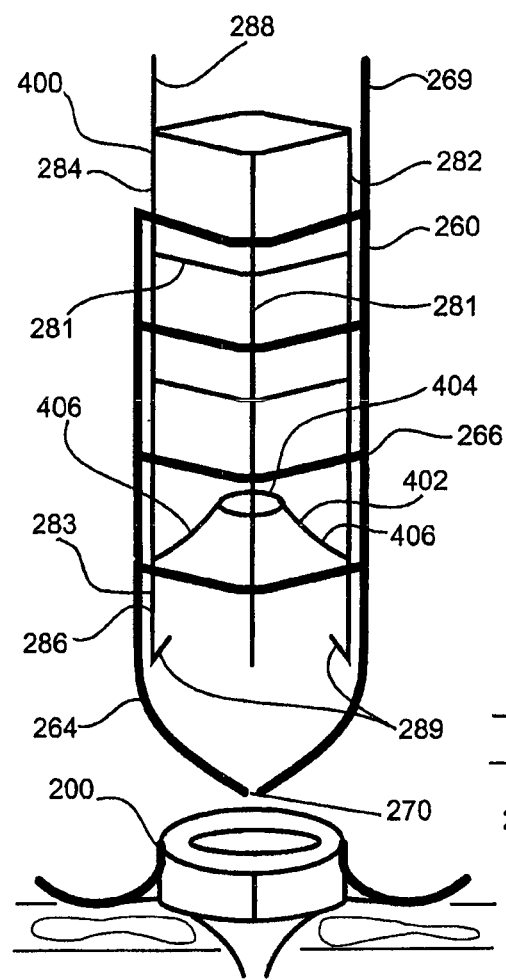
FIG. 18 is a schematic perspective view of any of the first to fourth embodiments of the invention prior to dismounting from a patient's muscle/fascia using the second arrangement of the extractor.
Figure 19:
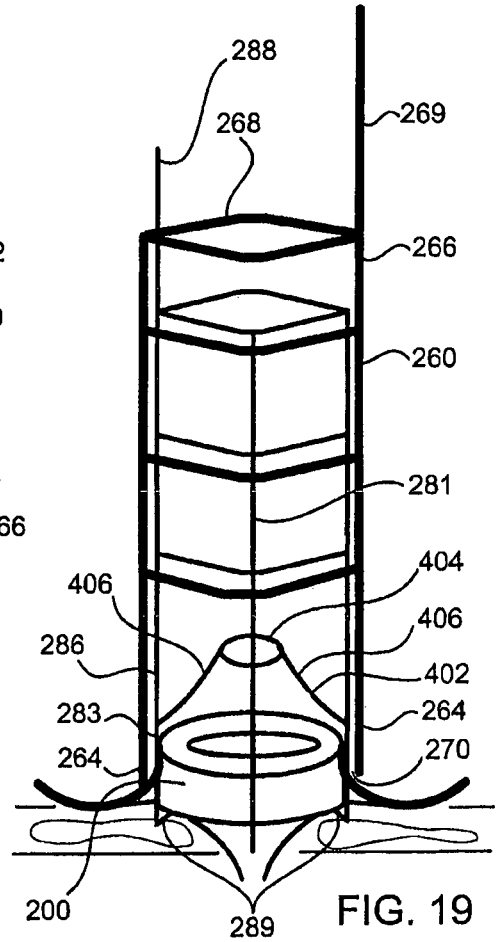
FIG. 19 is a schematic perspective view of any of the first to fourth embodiments of the invention during dismounting from a patient's muscle/fascia using the second arrangement of the extractor.
Figure 20:
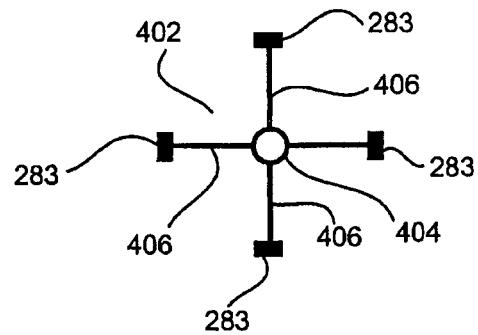
FIG. 20 is a schematic top view of an expansion system used for expanding the distal end of the second arrangement of the extractor.

FIGS. 18 to 20 show an alternative arrangement of an extractor 400 for extracting the access port 200 or 300 from the access hole 89. The extractor 400 may be used in conjunction with the applicator 260 or with the sheath 290 for extraction of the access port 200 or 300.

The extractor 400 according to the alternative arrangement has some similarities to the extractor 280 and similar reference numerals are used to identify similar parts.

The extractor 400 comprises a proximal rigid cylindrical body 282 and a distal expandable body 286. In arrangement, the distal expandable body 286 is hingedly attached to the proximal rigid cylindrical body 282. A handle 288 is attached to the proximal end of the proximal rigid cylindrical body 282. The distal end 286 comprises a plurality of barbs 289. As will be described with reference to the method for extracting the access port 200 or 300, the barbs 289 are adapted to grab the access port 200 or 300.

The proximal cylindrical body 282 of the extractor 400 is a rigid cylinder. The distal end 286 of the extractor 400 comprises resilient material. The extractor 400 may be manufactured from metal or plastic, among other suitable materials.

The fact that the distal end 286 comprises resilient material allows the distal end 286 of the extractor 400 to be expanded from a contracted condition to an expanded condition. In the expanded condition, the distal end 286 of the extractor 400 has a larger diameter than when the distal end 286 of the extractor 400 is in the contracted condition. As will be described with reference to the method for extracting the access port 200 or 300, the fact that the diameter of the distal end 286 of the extractor 400 can be varied facilitates grasping of the access ports 200 or 300.

The extractor 400 comprises an expander system 402. The expander system 402 is located at the distal end 286 of the extractor 400. The expander system 402 is adapted to expand the diameter of the distal end 286 of the extractor 400. The expander system 402 may be activated by a finger.

The expander system 402 comprises a centre 404 and a plurality of arm members 406 extending outwardly from the centre 404. The arrangement shown in FIG. 20 shows the expansion system 402 having four arm members 406. The arm members 406 surround the centre 404 at spaced locations with respect to each other. Each arm member 406 comprises an end attached to the centre 404 and an end attached to the longitudinal cage struts 283 of the extractor 400.

The arm members 406 comprise resilient material. This allows the arm members 406 to bend and thereby convert the downward force applied by a finger to a lateral force that separates the longitudinal cage struts 283 radially, thereby expanding the distal end 286 of the extractor 400.

As mentioned before, the expander system 402 allows expansion of the distal end 286 of the extractor 400. The expansion of the distal end 286 is accomplished by pushing the centre 404 of the expansion system 402 via a finger. Pushing the centre 404 resiliently deforms the arms 406 from the non deformed condition to the deformed condition. The arms 406 in the deformed condition expands the distal end 286 of the extractor.

The method for removing the access port 200 or 300 is shown in FIGS. 18 and 19. The present method utilizes the applicator 260 in conjunction with the extractor 400. However, as mentioned before, the access port 200 or 300 may be extracted using the sheath 290.

Also, the following descriptions of the method for removing the access port will be made with reference to the access port 200 in accordance to the third embodiment of the invention. However, the method for removing the access port 200 can be applied to any of the access ports in accordance to the first to fourth embodiments of the invention. Also, the method can be used for other types of ports used during gastric band surgical procedures and other procedures and other implant devices.

As previously explained, initially, an incision is made in the patient's body. The incision may be at the location where the incision was previously made during placement of the access port 200 which now will be removed or replaced. The depth of the incision must be such as to provide access to the access port 200 to be removed.

After the incision has been made, the extractor 400 is located superficial to the access port 200. This is accomplished by inserting the extractor 400 into the applicator 260. The applicator 260, including the extractor 400, is introduced into the incision and delivered to the access port 200.

The distal end 286 of the extractor 400 is expanded and this simultaneously expands the surrounding conical portion 264 of the applicator 260 while the extractor 400 is located immediately superficial to the access port 200. The distal end 286 of the extractor 400 is expanded through the expander system 402. The expander system 402 expands the distal end 286 by pressing with a finger the centre 404 of the expander system 402. The distal end 286 is returned to the contracted condition by releasing the pressure which is applied by finger on the centre 404.

In the expanded condition, the extractor 400 is mounted on the access port 200 allowing attachment of the barbs 289 to the lower portion 11b of the access port 200 (see FIG. 16). After attaching the barbs 289 to the lower portion 11b, the diameter of the distal end 286 extractor 400 may be reduced in order that the barbs 289 are secured to the access port 200. In this manner, the extractor 400 is releasable attached to the access port 200. The diameter of the distal end 286 of the extractor 400 is reduced by withdrawing the finger pressure on the expander system 402.

At this stage, the access port 200 can be extracted from the access hole 89. This is accomplished by pulling the extractor 400 in order to draw the access port 200 (together with the stabilisers 210 and membrane 238, if the membrane 238 is included) into the applicator 260. Once the access port 200 (together with the stabilisers 210 and membrane 238, if the membrane 238 is included) is contained in the applicator 260, the applicator 260 may be extracted from the patient's body by pulling the handle 269 of the applicator 260 in order to retrieve the applicator 260 containing the extractor 400 and the access port 200.

Modifications and variations as would be apparent to a skilled addressee are deemed to be within the scope of the present invention.

For example, the stabilisers 210 may be retrofitted to any type of access ports or surgical devices to be implanted in a body of a patient. For this, the stabiliser 210 comprise attachment means for attaching the stabilisers 210 to the access ports or surgical devices to be implanted in a body of a patient.

Further, it should be appreciated that the scope of the invention is not limited to the scope of the embodiments disclosed. Throughout the specification and claims, unless the context requires otherwise, the word "comprise" or variations such as "comprises" or "comprising", will be understood to imply the inclusion of a stated integer or group of integers but not the exclusion of any other integer or group of integers.

The claim defining the invention is as follows:

1. An access port comprising a port body comprising an upper portion and a lower portion being of resilient construction and configured to define a plug formation of tapered configuration for embedment into a hole in the body of a patient for closure of the hole, and a catheter, the port body defining a cavity into which a fluid can be delivered or from which a fluid can be extracted through one side of the port body, the catheter having a proximal end being disposed on the lower portion of the port body and in fluid communication with the cavity, wherein the lower portion being of resilient construction defines a flexible connection between the catheter and the port body permitting non-axial movement of the catheter with respect to the upper portion of the port body.

2. The access port according to claim 1 wherein said one side of the body is adapted to receive an adjustment needle for delivery of the fluid into the cavity.

3. The access port according to claim 2 wherein the port body is adapted to protect the catheter from the adjustment needle.

4. The access port according to claim 2 wherein the body portion comprises a barrier to limit the depth to which a needle can penetrate into the port.

5. The access port according to claim 4 wherein the barrier is positioned within the cavity between said one side of the port body and an opposite side of the port body.

6. The access port according to claim 4 wherein the barrier comprises a barrier plate supported in spaced relation with respect to the lower portion of the port body.

7. The access port according to claim 6 wherein the barrier plate comprises a plate formed of metal or any other appropriate hard material.

8. The access port according to claim 1 wherein said one side is adapted for extraction of the fluid through said one side.

9. The access port according claim 1 wherein the port body comprises a compartment having a self-sealing portion which can be penetrated by an adjustment needle for delivery of fluid to the cavity or for extraction of fluid from the cavity.

10. The access port according to claim 1 wherein the port body comprises an outlet on the lower portion which communicates with the cavity and from which the catheter extends.

11. The access port according to claim 1 wherein the hole comprises a laparoscopic access hole in the muscle/fascia of the patient.

12. The access port according to claim 1 wherein the lower portion of the body is adapted to close holes of various sizes.

13. The access port according to claim 1 wherein the flexibility of the lower portion of the port body increase axially along the longitudinal axis of the lower portion.

14. The access port according to claim 1 wherein the port body comprises integral means for anchoring the port body to the body of the patient.

15. An access port comprising a port body comprising an upper portion and a lower portion being of resilient construction and configured to define a plug formation of tapered configuration for embedment into a hole in the body of a patient for closure of the hole, and a catheter, the port body defining a cavity into which a fluid can be delivered or from which a fluid can be extracted through one side of the port body, the catheter having a proximal end attached to the lower portion of the port body and in fluid communication with the cavity, wherein the lower portion being of resilient construction defines a flexible connection between the catheter and the port body permitting non-axial movement of the catheter with respect to the upper portion of the port body.

16. The access port according to claim 15 wherein the flexibility of the flexible connection between the port body and the catheter increases progressively in the direction away from the port body.

17. The access port according to claim 15 wherein the port body is adapted to close holes of various sizes.

18. The access port according to claim 15 wherein the hole comprises a laparoscopic access hole in the muscle/fascia of the patient.

19. The access port according to claim 15 wherein the port body comprises integral means for anchoring the port body to the body of the patient.

20. An access port comprising a port body having a first side and a second side in opposed relation, and a catheter disposed on the second side to receive and convey the fluid, the first side of the port body being adapted to receive an adjustment needle for delivery or extraction of a fluid, the second side of the body is of resilient construction and is configured to define a plug formation of tapered configuration for embedment into a hole in the body of a patient for closure of the hole, wherein the second side of the body being of resilient construction defines a flexible connection between the catheter and the port body permitting non-axial movement of the catheter with respect to the first side of the port body.

21. The access port according to claim 20, wherein the flexibility of the second side of the port body increase axially along the longitudinal axis of the second side.

* * * * *